US011740344B2

(12) United States Patent
Chun et al.

(10) Patent No.: US 11,740,344 B2
(45) Date of Patent: Aug. 29, 2023

(54) DYNAMICAL OBJECT ORIENTED INFORMATION SYSTEM FOR SUSTAINING VITALITY OF A TARGET SYSTEM

(71) Applicant: HANKOOKIN, INC., Raleigh, NC (US)

(72) Inventors: James Jiwen Chun, Raleigh, NC (US); Andrew Youngho Chun, Raleigh, NC (US); Angela Soyoung Chun, Raleigh, NC (US); Jennifer Miseong Chun, Raleigh, NC (US)

(73) Assignee: HANKOOKIN, INC.

( * ) Notice: Subject to any disclaimer, the term of this patent is extended or adjusted under 35 U.S.C. 154(b) by 153 days.

(21) Appl. No.: 16/585,881

(22) Filed: Sep. 27, 2019

(65) Prior Publication Data

US 2020/0103514 A1 Apr. 2, 2020

Related U.S. Application Data

(60) Provisional application No. 62/737,123, filed on Sep. 27, 2018.

(51) Int. Cl.
*G01S 13/06* (2006.01)
*G05B 13/02* (2006.01)
(Continued)

(52) U.S. Cl.
CPC .......... *G01S 13/06* (2013.01); *G05B 13/0265* (2013.01); *G06F 1/26* (2013.01);
(Continued)

(58) Field of Classification Search
CPC .... G01S 13/06; G16H 30/20; G05B 13/0265; G06F 1/26; G06F 11/3058; G06F 11/3495; G05D 1/0088
(Continued)

(56) References Cited

U.S. PATENT DOCUMENTS 6,671,818 B1 12/2003 Mikurak
2002/0062077 A1 5/2002 Emmenegger et al.
(Continued)

FOREIGN PATENT DOCUMENTS

EP 1988499 A1 11/2008
WO 2018108717 A1 6/2018
WO WO-2020106364 A3 * 7/2020

OTHER PUBLICATIONS

Density optimized multi-node server for extreme compute at scale, Dell EMC PowerEdge C6520 Spec Sheet, Feb. 2021, Dell Technologies.
(Continued)

*Primary Examiner* — Michael P Nghiem
(74) *Attorney, Agent, or Firm* — Ashok Tankha

(57) ABSTRACT

A method for monitoring and sustaining vitality of a target system (TS) dynamically by providing an object oriented information system (OOIS) for TS, receiving and monitoring information of surrounding environment of TS and information within TS by sensory units; creating received and monitored information wave packets (RMIWP); transform RMIWP into one or more processed information wave packets (PIWP) by translating frequencies of RMIWP into a common frequency; storing PIWP in ordered time sequence, space and logical classifications; recognizing strategic events (SE) based on stored PIWP, refining details of SE, recognizing a criteria for maximum vitality of TS, recognizing future plans (FP) based on SE and evaluating vitality of OOIS and recognizing a FP with maximum vitality, converting FP into steps in time and space for a motor unit for moving TS, monitoring movement of TS, comparing outcome with the criteria, and dynamically selecting a FP with maximum vitality.

21 Claims, 16 Drawing Sheets

(51) Int. Cl.
*G06F 1/26* (2006.01)
*G06F 11/30* (2006.01)
*G06F 11/34* (2006.01)
*G16H 30/20* (2018.01)
*G05D 1/00* (2006.01)

(52) U.S. Cl.
CPC ...... *G06F 11/3058* (2013.01); *G06F 11/3495* (2013.01); *G16H 30/20* (2018.01); *G05D 1/0088* (2013.01)

(58) Field of Classification Search
USPC .......................................................... 702/150
See application file for complete search history.

(56) References Cited

U.S. PATENT DOCUMENTS

| | | |
|---|---|---|
| 2003/0061004 A1 | 3/2003 | Discenzo |
| 2009/0018935 A1* | 1/2009 | Neumaier .............. G06Q 40/12 705/30 |
| 2010/0287421 A1 | 11/2010 | Golowner et al. |
| 2013/0013348 A1 | 1/2013 | Ling et al. |
| 2015/0206339 A1* | 7/2015 | Chun .................... G06T 15/205 345/419 |
| 2015/0310279 A1 | 10/2015 | Bare et al. |
| 2019/0369616 A1* | 12/2019 | Ostafew ............ B60W 60/0027 |
| 2020/0273268 A1* | 8/2020 | Bhattacharyya ........ H04W 4/40 |
| 2021/0323669 A1* | 10/2021 | Skaarup ............... G05D 1/0088 |

OTHER PUBLICATIONS

II 900/II910 Acoustic Imager, Product Specifications, Apr. 2019 Rev. B 9/20, Fluke Corporation.
Family 0207+01 IBM Blue Gene/Q Supercomputer, 2021, IBM Corporation.
QPU-Specific Physical Properties: DW_2000Q_6, Nov. 19, 2012, D-Wave User Manual 09-1215A-C, D-Wave Systems Inc.
Adapta™ DR Pacing System, Models ADDR01, ADDRO3, ADDR06, ADDRS1, ADDRL1, Medtronic Adapta, 2017, Medtronic.
Shadow Dexterous Hand Technical Specification, Feb. 2021, Shadow Robot Company.
ENVG-B Enchanced Night Vision Goggle-Binocular, Aug. 2021, L3HARRIS.
Natural Language Client Libraries, Cloud Natural Language API, Google Cloud., Nov. 15, 2016.
Grasshopper-New in Rhino 6, Rhinoceros, Jan. 30, 2018.
Intel Core i51135G7 Processor 8M Cache up to 4.20 GHz Product Specifications, Intel., 3rd quarter of 2020.

* cited by examiner

DYNAMICAL OBJECT ORIENTED INFORMATION SYSTEM FOR SUSTAINING VITALITY OF A TARGET SYSTEM

CROSS-REFERENCE TO RELATED APPLICATIONS

This application claims priority to and the benefit of the provisional patent application titled "Dynamical Object Oriented Information System To Sustain Vitality Of A Target Device", application No. 62/737,123, filed in the United States Patent and Trademark Office on Sep. 27, 2018. The specification of the above referenced patent application is incorporated herein by reference in its entirety.

BACKGROUND

Earlier systems, such as, an image processing system (IPS) comprise a computer implemented method for constructing and rendering an object oriented image (OOI) of a target object in an original spatial position and orientation of the target object. While recording an image of a target object, the IPS records extended image data (EID); for example, spatial coordinates of an image recording device (IMR), multi-dimensional position and orientation of a line of vision of the IMR and the target object, etc. The IPS determines the original spatial position and orientation of the target object from the EID, constructs the OOI of the target object by repositioning and reorienting the recorded image based on the original spatial position and orientation of the target object, and renders the constructed OOI on an image display device. For constructing a three dimensional OOI, the IPS records multiple images and the EID of the target object at multiple orientations. The above mentioned system uses original spatial position and orientation of the target system in time domain to maintain vitality of the device.

Many systems and devices actively interact with the surrounding environment. Similar to a living organism that continuously senses and exerts action over itself and its environment, these systems and devices, hereafter referred to as target systems, are also influenced by the surrounding environment and accordingly alter their vital activities and interactions with their surrounding environment. Consider an unmanned automobile electronic device (UAED) as an example of a target system. Examples of activities and interactions related to the unmanned automobile electronic device (UAED) comprise vital activities comprising audio, visual, tactile and mobile interactions. Vital activities on the target system can be analyzed in time and space. Usually, the vital activities, the shape and form of the target system and the information stored inside the target system are required to be sustained over planned amount of time and space. For example, the UAED is required to sustain its vital activities over time and space via programmed activities and mobility. The analysis of vital activities of a target system has multiple factors that influence the sustainability of the target system. The shape and form of the target system could be altered by physical impact, water intrusion, chemical contamination, interaction with heat, electromagnetic waves, etc. The information in the target system is also affected when a hacker hacks into the target system and alters the information. In the case of the UAED, one of the crucial factors that the UAED depends on is external electrical energy that is needed to perform and sustain the UAED's vital activities. If the electrical energy of the device were to run out, active activities of the device would stop and the device loses its vitality.

Hence, there is a long felt but unresolved need for dynamical object oriented information system to sustain vitality of a target system, for example, the unmanned automobile electronic devices (UAED) by extending beyond the original spatial position and orientation of the target system and into the time domain to maintain vitality of the target system. There is a need for a system that continuously analyzes the vital activities of the target system as the object that sustains electricity, and develops programmed mobile activities to gain energy, as well as avoid physical impacts, foreign contamination, unwanted radiation, and internal intrusions. There is also a need for a system that provides mobility or prompts the target system to move and access energy sources and escape from potential dangers. There is also a need for a system that denies access to information inside the target system. There is also a need for a system that reduces stress experienced by humans engaged in labor intensive activities using machines.

SUMMARY OF THE INVENTION

This summary is provided to introduce a selection of concepts in a simplified form that are further disclosed in the detailed description of the invention. This summary is not intended to determine the scope of the claimed subject matter.

The method and object oriented information system (OOIS) disclosed herein address the above recited need for monitoring and sustaining vitality of a target system dynamically. The OOIS disclosed herein continuously analyzes the vital activities of the target system, and develops programmed mobile activities for the target system to gain energy, as well as avoid physical impacts, foreign contamination, unwanted radiation, and internal intrusions. The OOIS provides mobility or prompts the target system to move and access energy sources and escape from potential dangers. The OOIS denies access to information inside the target system. The OOIS reduces stress experienced by humans engaged in labor intensive activities using machines.

The OOIS comprises a non-transitory computer readable storage medium configured to store computer program instructions defined by units of the OOIS and at least one processor communicatively coupled to the non-transitory computer readable storage medium. The at least one processor is configured to execute the defined computer program instructions. The OOIS further comprises multiple sensory units, a dynamic commanding center unit (DCC), a central storage in time unit (CST) comprising a layered mapping system in time unit (LMST), a central storage in space unit (CSS) comprising a layered mapping system in space unit (LMSS), and a rhythmic power unit (RPU) for providing rhythmic power to the sensory units, the DCC, the CST, and the CSS. The sensory units comprise a tactile unit, a visual unit, and an audio unit.

The method comprises providing the object oriented information system (OOIS) for the target system. The method comprises receiving rhythmic waves that have traversed a target system and obtaining information of the surrounding environment of the target system and the information within the target system from the traversed rhythmic waves by the sensory units. The sensory units create one or more received information wave packets using the received information of the surrounding environment of the target system and the information within the target system. The method further comprises communicating the received information wave packets to the DCC by the sensory units.

The method further comprises transforming the received information wave packets into one or more processed information wave packets by the DCC by translating frequencies of the received information wave packets into a common frequency.

The method further comprises storing the one or more processed information wave packets in an ordered time sequence and collecting feedback central storage in time wave packets by the central storage in time unit comprising the layered mapping system in time unit. The method further comprises storing the one or more processed information wave packets based on logical classifications and collecting feedback central storage in space wave packets by the central storage in space unit comprising the layered mapping system in space unit. The method further recognizing one or more strategic events based on the stored processed information wave packet in the central storage in time unit and the processed information wave packet in the central storage in space unit. Next, details of the recognized strategic events are refined by the dynamic commanding center unit and a criteria for evaluating maximum vitality of the target system based on time and spatial configuration of the target criteria is recognized. Further, one or more future plans are recognized based on the generated strategic events and on evaluating vitality of the object oriented information system based on the criteria for each of the one or more future plans. The method further comprises recognizing a future plan from the recognized one or more future plans with maximum vitality of the target system based on the criteria.

The method further comprises converting the recognized future plan into multiple steps in time and space, and providing the steps to a motor unit configured for moving the target system. The method further comprises monitoring discrete individual events by the sensory units during the movement of the target system. The, outcome of the discrete individual events is compared with the criteria to evaluate the vitality of the target system. Further, an alternative future plan is dynamically selected based on the comparison. The dynamically selected alternative future plan is either the selected future plan or a new future plan.

In one or more embodiments, related systems comprise circuitry and/or programming for effecting the method disclosed herein. The circuitry and/or programming can be any combination of hardware, software, and/or firmware configured to effect the method disclosed herein depending upon the design choices of a system designer. Also, in an embodiment, various structural elements can be employed depending on the design choices of the system designer.

BRIEF DESCRIPTION OF THE DRAWINGS

The foregoing summary, as well as the following detailed description of the invention, is better understood when read in conjunction with the appended drawings. For the purpose of illustrating the invention, exemplary constructions of the invention are shown in the drawings. However, the invention is not limited to the specific method and components disclosed herein. The description of a method step or a component referenced by a numeral in a drawing is applicable to the description of that method step or component shown by that same numeral in any subsequent drawing herein.

DETAILED DESCRIPTION OF THE INVENTION

Figure 1:
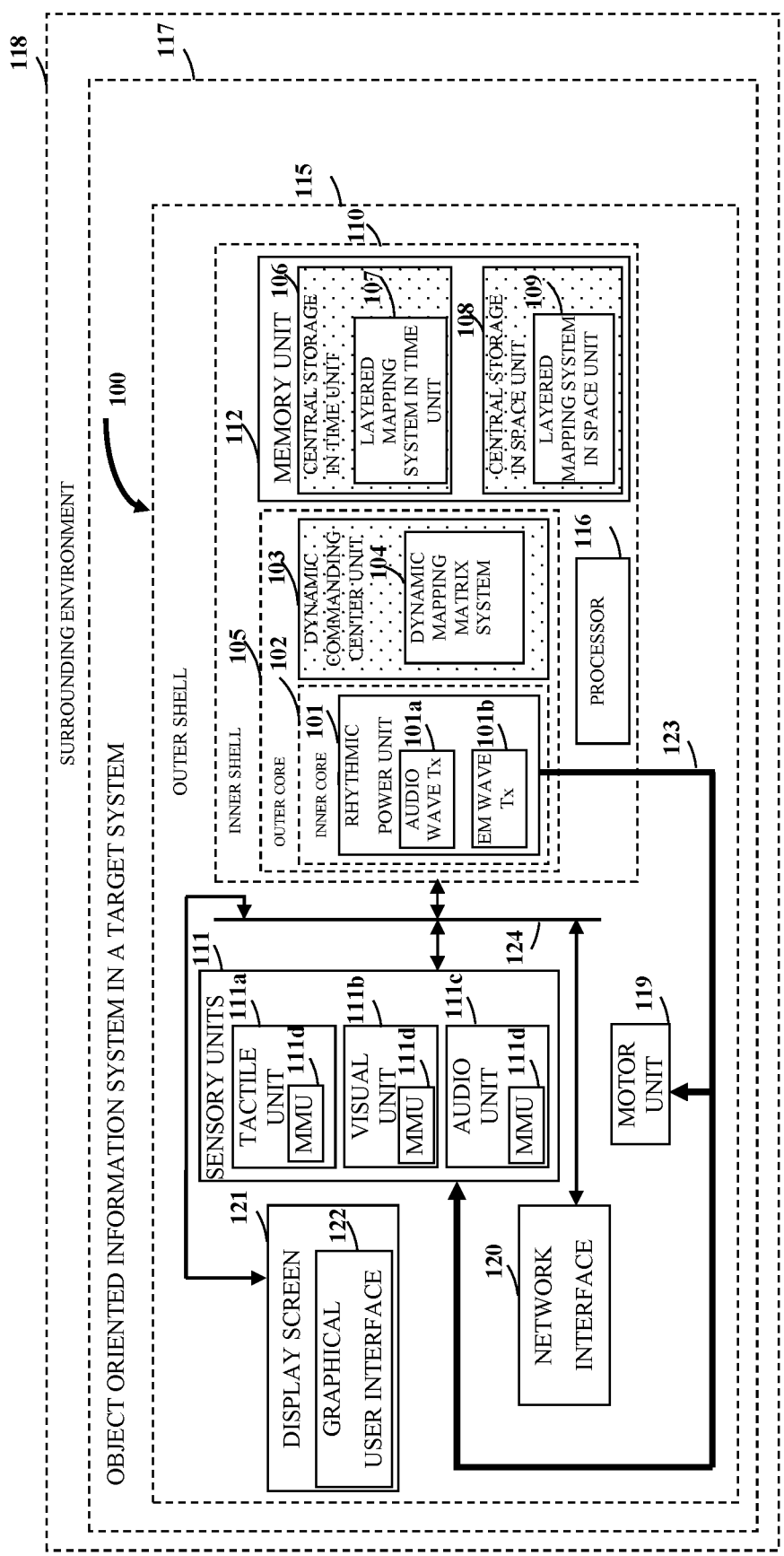
FIG. 1 exemplarily illustrates layers of an object oriented information system in a target system along with a surrounding of the target system.

FIG. 1 exemplarily illustrates layers of an object oriented information system (OOIS) 100 in a target system 117 along with a surrounding environment 118 of the target system 117. The OOIS 100 monitors and sustains the vitality of the target system 117 dynamically. As used herein, the target system 117 refers to any machine comprising electrical, electronic, mechanical, and electromechanical components. Examples of the target system 117 comprise a lawnmower, unmanned aerial vehicle (UAV), an electric car, etc. As used herein OOIS 100 is a device that is fitted to the target system 117 in order to monitor and sustain vitality of the target system 117 dynamically. As used herein, waves refer to electromagnetic waves including radio waves, microwaves, infrared, (visible) light, ultraviolet, X-rays, and gamma rays. As used herein, the waves also refer to sound waves, pulsed waves of electrical current. As used herein, the waves also refer to matters and activities that happen in rhythmic cycles, for example, daily activities. As used herein, units of the target system 117 refer to parts, functional units, and components of the target system 117. One or more units of the target system 117 form clusters.

In an embodiment, the object oriented information system (OOIS) 100 is a Raspberry Pi® processor 116 based single-board computer comprising a non-transitory computer readable storage medium 112. The non-transitory computer readable storage medium 112 is configured to store computer program instructions defined by units of the OOIS 100. The processor 116 is communicatively coupled to the non-transitory computer readable storage medium 112. The processor 116 is configured to execute the defined computer program instructions. The OOIS 100 further comprises multiple sensory units 111, a dynamic commanding center unit (DCC) 103, a central storage in time unit (CST) 106 comprising a layered mapping system in time unit (LMST) 107, a central storage in space unit (CSS) 108 comprising a layered mapping system in space unit (LMSS) 109, and a rhythmic power unit (RPU) 101. The RPU 101 also provides rhythmic power to the sensory units 111, the DCC 103, the CST 106, and the CSS 108. The sensory units 111 comprise a tactile unit 111a, a visual unit 111b, and an audio unit 111c. In an embodiment, the RPU 101 transmits rhythmic electromagnetic waves and rhythmic audio waves, hereafter rhythmic waves within the target system 117.

The target system 117 interacts with the surrounding environment. The target system 117 is also influenced by the surrounding environment 118 and accordingly alters its vital activities and interactions with its surrounding environment 118. Vital activities of the target system 117 can be analyzed in time and space. The object oriented information system (OOIS) 100 sustains the vital activities, the shape and form of the target system 117 and the information stored inside the target system 117 over a planned amount of time and space. For example, a target system 117, such as an unmanned automobile electronic device (UAED) sustains its vital activities over time and space using programmed activities and mobility produced by OOIS 100.

The analysis of vital activities of a target system 117 has several factors that influence the sustainability of the target system 117. In an embodiment, the shape and form of the target system 117 is altered by physical impact, water intrusion, chemical contamination, interaction with heat, electromagnetic waves, etc. The information inside the target system 117 can be altered by intrusion of hackers leading to unwanted access to information of the target system 117 and alteration of the accessed information. In the case of the unmanned automobile electronic device (UAED), one factor this target system 117 depends on is the external sources such as electrical energy that is required to perform and sustain its vital activities. If the electrical energy of the UAED were to run out, active activities of the UAED would stop and the UAED will lose its vitality. Thus, the OOIS 100 analysis of vital activities regards the UAED as the target system 117 that will sustain its electricity, and develops programmed mobile activities to gain energy, as well as avoid physical impacts, foreign contamination, unwanted radiation, and internal intrusions. Mobile activities produced by the OOIS 100 analysis enables the target system 117 to access an energy source, escaping from potential dangers, and perform actions that deny access to information inside the target system 117.

To perform object oriented information system (OOIS) 100 analysis, physical and information status of the target system 117 and the surrounding environment 118 of the target system 117 are defined as continuous events in time domain, similar to waves. The continuous events are specified at a particular time as discrete spatial properties of the OOIS 100 analysis of the target system 117. The vitality of the target system 117 is a complete vital cycle (VC) of events. The target system 117 comprises a cluster of smaller parts or units and each cluster of smaller parts or units comprises its own events that work together to complete the VC of the target system 117. For example, if the target system 117 is an object oriented self-precision driven mechanical system, for example, a robotic lawn mower, the robotic lawn mower comprises an engine, a transmission, wheels, chassis, grass cutting mechanism, steering mechanism etc. The engine of the robotic lawn mower is considered as a cluster having its own set of smaller parts comprising cylinders, fuel pump, etc. Similarly, the transmission is considered as a cluster having its own set of smaller parts comprising gears, clutch, etc.

Furthermore, each small part in the cluster comprises own cycle of activities that are characterized as their own intrinsic rhythms (IR). The VC of the target system 117 is divided into multiple smaller intervals in the time domain. Each interval is measurable and also predictable in time, therefore each small part in the cluster implements long term planning at future steps for correcting themselves to meet a final goal. In an embodiment, the vital activities of the target system 117 comprise variables. The variables comprise rhythmic wave received as input by the sensory units 111, where the rhythmic wave has traversed the target system 117. The variables also comprise inherent cycles of activities of the units, i.e., parts of the target system 117. The variables also comprise the vitality of the target device 117 and division of the vitality in time domains. The variables exhibit wave properties. Due to the wave nature of the variables, the variable undergo continuous rhythmic changes in time and do not stay in a single position in space and instead, expand in each direction in the space. The rhythmic waves overlap with each other and create observable spatial patterns that can be described and measured as ordered scalar values. The ordered scalar values of the rhythmic waves comprise the wave cycles that are described as a natural number, magnitude of wave forms, and rate of expansion of the rhythmic waves in space. Furthermore, the rhythmic waves interact with surrounding medium that alters the properties of the rhythmic waves.

The rhythmic waves undergo one or more common wave phenomena comprising reflection, refraction, diffraction, interference, polarization, dispersion, and absorption in the target system 117. Thus, the waves evolve when they are transmitted by the RPU 101. With respect to the vital activities of the target system 117, the events are packets of wave with various frequencies called wave packets (WP). The magnitude of the rhythmic waves also exhibit observable patterns at particular points in space and time called digitized wave points (DWP). The evolving rhythmic waves form packets of wave (herein referred to as wave packets or WP) that are digitally represented by the digitized wave points (DWP). It is possible to evaluate and analyze properties of the rhythmic wave comprising patterns, forms and phases using the values of DWP. Although the final form of the wave packet (WP) looks chaotic and different from the original rhythmic wave forms from which the wave packet originated, it is possible to propagate backwards and trace the wave packet to its original rhythmic wave form. Continuation of wave in infinitely dividable increments in time is represented as discrete points in time as DWP. The waveforms in WP described as DWP comprise dynamic correlation between structure and geometries of objects in the target system 117. The DWPs from different waves overlap with each other and the overlap results in addition or subtraction to form WP in time and space. The DWPs are used to analyze and characterize the WP in the OOIS 100, describing state and the events of the target system 117 with quantified values at each particular time, and the spatial location or orientation. The coordinate system used in the DWP is based on objective coordinates of the target system 117. The wave is an intrinsic property of time, space and the surrounding medium; however upon constraining in confinement, the wave evolves into WP that also carries information about the confinement. The possible collection of the frequencies of the WP is determined by boundaries of the confinement, and selections of the frequencies from the collection of the frequencies of the WP that are generated are based on timing, spatial properties and energy state of the events. The rhythms or the frequencies in the WP can be viewed in frequency spectrum of the WP. The WP exhibits chaos like patterns with the waves mixed in time and space. The waves with same frequencies, multiples or exact divisions of the frequency of the wave resonates with each other in time when the waves are overlapped in phase and space and form notable wave patterns.

In an embodiment, the OOIS 100 comprises a non-transitory computer readable storage medium 112 configured to store computer program instructions defined by units of the object oriented information system (OOIS) 100 and at least one processor 116 communicatively coupled to the non-transitory computer readable storage medium 112. The processor 116 is configured to execute the defined computer program instructions. The OOIS 100 further comprises multiple sensory units 111, a dynamic commanding center unit (DCC) 103, a central storage in time unit (CST) 106 comprising a layered mapping system in time unit (LMST) 107, a central storage in space unit (CSS) 108 comprising a layered mapping system in space unit (LMSS) 109, and a rhythmic power unit (RPU) 101 for providing rhythmic power to the sensory units 111, the DCC 103, the CST 106, and the CSS 108. The sensory units 111 comprise a tactile unit 111a, a visual unit 111b, and an audio unit 111c. In an embodiment, the OOIS 100 further comprises a display screen 121 comprising a graphical user interface 122 for allowing a user to program the OOIS 100. In an embodiment, the display screen 121 is located on an outer shell 115 of the OOIS 100.

In the object oriented information system (OOIS) analysis of the target system 117, the OOIS 100 is installed inside the target system 117. In an embodiment, the OOIS 100 is installed on an outer surface of the target system 117. In another embodiment, the OOIS 100 is located remotely from the target system 117 with the sensory units 111, motor unit 119 and the RPU 101 located in the target system 117. The remotely located OOIS 100 also comprises an RPU 101.

The rhythmic power unit (RPU) 101 is configured to transmit rhythmic waves within the target system 117. In an embodiment, as exemplarily illustrated in FIG. 1, the RPU 101 comprises an Audio wave transmitter (Audio wave Tx) 101a for transmitting the rhythmic audio waves and an Electromagnetic wave transmitter (EM wave Tx) 101b for transmitting the electromagnetic audio waves. In another embodiment, the rhythmic audio waves are transmitted by the audio unit 111c, and the rhythmic electromagnetic waves are transmitted by one or more of the tactile unit 111a and the visual unit 111b. In an embodiment, the rhythmic audio waves and the rhythmic electromagnetic waves are transmitted by one or more transmitters (not shown) of the audio unit 111c, the tactile unit 111a, and the visual unit 111b that are spatially separated from the audio unit 111c, the tactile unit 111a, and the visual unit 111b. In an embodiment, the Audio wave Tx 101a and the EM wave Tx 101b transmit the rhythmic waves to the audio unit 111c, the tactile unit 111a, and the visual unit 111b for transmission by the one or more transmitters (not shown) of the audio unit 111c, the tactile unit 111a, and the visual unit 111b. In another embodiment, the Audio wave Tx 101a and the EM wave Tx 101b transmit the rhythmic waves directly using transmitters (not shown) located at several locations within the target system 117.

The transmitted rhythmic waves traverse the inside of the target system 117 and the surrounding environment 118 of the target system 117. The sensory units 111 receive the rhythmic waves that have traversed the target system 117. The sensory units 111 obtain information of the surrounding environment 118 of the target system 117 and information from within the target system 117 from the traversed rhythmic waves. The sensory units 111 create one or more received information wave packets. The sensory units 111 also monitor the target system 117 using the received information of the surrounding environment 118 of the target system 117 and the information within the target system 117.

The dynamic commanding center unit (DCC) 103 transforms the received information wave packets into one or more processed information wave packets by translating frequencies of the received information wave packets into a common frequency. The central storage in time unit (CST) 106 comprising the layered mapping system in time unit (LMST) 107 stores the processed information wave packet received from the DCC 103 unit in an ordered time sequence and collects feedback central storage in time wave packets. The CSS 108 comprising the LMSS 109 for storing the processed information wave packet from the DCC 103 based on logical classifications and collects feedback central storage in space wave packets.

The processor 116 recognizes one or more strategic events based on the stored processed information wave packet in the central storage in time unit (CST) 106 and the processed information wave packet in the central storage in space unit (CSS) 108. The DCC 103 refines details of the recognized strategic events. The processor 116 also recognizes a criteria for evaluating the maximum vitality of the target system 117 based on time and spatial configuration of the target system 117. The processor 116 also recognizes one or more future plans based on the recognized strategic events and on evaluating vitality of the target system 117 based on the criteria for each of the one or more future plans. The processor 116 also recognizes a future plan from the recognized one or more future plans with maximum vitality of the target system 117 based on the criteria. The processor 116 also converts the recognized future plan into multiple steps in time and space and provides the steps to the motor unit 119. The motor unit 119 moves the target system 117 based on the steps.

The sensory units 111 monitor discrete individual events associated with the target system 117 during the movement of the target system 117. The processor 116 then compares the outcome of the discrete individual events with the criteria to evaluate the vitality of the target system 117. Next, the processor 116 dynamically selects an alternative future plan based on the comparison. The alternative future plan is one of the selected future plan and a new future plan.

In the object oriented information system (OOIS) analysis of the target system 117 described as layers of cycles of continuous waves divided into smaller intervals in the time domain. Each layer comprises multiple components and each component has physical dimensions, shape, and properties and intrinsic rhythms (IR) in the component's functionality. The OOIS 100 comprises layers, such as, inner core 102, outer core 105, inner shell 110, and outer shell 115. The inner core 102 comprises rhythmic power unit (RPU) 101. The RPU 101 provides energy to the OOIS 100, therefore the RPU 101 is within the inner core 102. The outer core 105 of the OOIS 100 comprises a dynamic commanding center (DCC) 103. The DCC 103 comprises a dynamical mapping matrix (DMM) 104 system for processing information. The DMM 104 processes large amount of information in short time durations. The DCC 103 is placed in the outer core 105 next to the RPU 101. The inner shell 110 of the OOIS 100 comprises central storage in time (CST) 106 and central storage in space (CSS) 108. The entire collection of information of the OOIS 100 is processed by the DCC 103 and stored in layered mapping system in time (LMST) 107 of the CST 106 and layered mapping system in space (LMSS) 109 of the CSS 108. The outer shell 115 of the OOIS 100 comprises the sensory units 111 comprising the tactile unit 111*a*, the visual unit 111*b*, and the audio unit 111*c*. The outer shell 115 of the OOIS 100 also comprises a motor unit (MU) 114. The surrounding environment 118 of the target system 117 is a finite space with which the OOIS 100 constantly interacts wherein boundaries are defined by the sensory units 111.

In an embodiment, the layers of the object oriented information system (OOIS) 100, i.e., the inner core 102, the outer core 105, the inner shell 110, and the outer shell 115 are insulated to shield the units in the OOIS 100 from electrical and electro-magnetic waves. The OOIS 100 comprises power transfer channels (PT) 123 and information transfer channels (IT) 124, as exemplarily illustrated in FIG. 1. In an embodiment, the power transfer channel (PT) 123 is used to transfer rhythmic power from the RPU 101 to the sensory units 111, the CST 106, the CSS 108, the DCC 103, the motor unit 119, and the plurality of sensory units 111. In an embodiment, the DCC 103 comprises multiple mini receptive units (MRU) 301 that form a mini receptive unit (MRU) matrix 300, as exemplarily illustrated in FIG. 3. In an embodiment, the power transfer channel (PT) 123 is used to transfer rhythmic waves from the RPU 101 to the transmitters of the sensory units 111. In another embodiment, the information transfer channel (IT) 124 is used to transfer rhythmic waves from the RPU 101 to the Audio wave Tx and the EM wave Tx. In an embodiment, the information transfer channels (IT) 124 transfer the one or more received information wave packets from the sensory units 111 to the DCC 103. Since the layers 102, 105, 110 and 115 are insulated, the rhythmic waves transmitted by RPU 101 are transmitted through the PT 123 and the one or more received information wave packets through the IT 124. In a confined space, for example, the inner shell 110, the waves comprise the information of the surrounding environment 118 of the target system 117 and information from within the target system 117 and the CST 106 finds the highest of the resonating rhythmic wave that has traversed the target system 117, and the highest of the resonating rhythmic wave becomes the dominating future plan (FP) in space and time. The FP is the highest dominating wave in the CST 106 and the central storage in space (CSS) 108 that determines the final state of the target system 117. The highest dominating wave comprises the information until the time for its formation, and is in harmony with the waves within the OOIS 100 and connects with each of the waves present. If there are changes in the waves, the changes are reflected instantaneously in the FP, and the resulting new FP reflects the new changes in the target system 117. The FP is in tune with the final goal, and the FP receives the information in the past and connects to the future in discrete steps in time. If there are changes in the target system 117, the FP changes. However, the final goal is maintained. If no changes occur, the current FP will bring the target system 117 a step closer towards the final goal. This describes spontaneous selection process of FP in the OOIS 100, for example in the processor 116.

The formation of the future plan (FP) is selective, converging and transient, ready to adapt and to change at any time. The FP creates a clear new state intrinsically directed towards the device and unifies information to the target system 117 and due to the wave nature of the information, the waves expands over space in each of the directions. The waves transmitted by the RPU 101 reflect when the waves encounter obstacles within the target system 117 and in the surrounding environment 118, and the waves refract i.e., change direction when the waves pass from one medium into a different medium having a depth, the waves diffract and interfere in close proximity, and polarize under the constrained field. Therefore, the waves transmitted by the RPU 101 undergo one or more of reflection, refraction, diffraction, polarization, absorption, interference and other wave phenomenon. Reflection is a wave phenomenon where a wave incident on a surface hits the surface and bounces off the surface. Diffraction is the wave phenomenon where the wave bends and spreads around an obstacle. Refraction is when waves change direction as they pass from one medium to another. Polarization is when a wave oscillates in one particular direction. Electromagnetic waves are often polarized using a polarizing filter. Only transverse waves can be polarized. However, longitudinal waves, such as sound, cannot be polarized because they always travel in the same direction of the wave. Absorption is when a wave comes into contact with a medium and causes the medium's molecules to vibrate and move. This vibration absorbs or takes some of the energy away from the wave and less of the energy is reflected. Interference occurs when one wave comes into contact with another wave. When the waves meet, the resulting wave will have the amplitude of the sum of the two interfering waves. Depending on the phase of the waves, the interference can be constructive or destructive. Constructive interference is a phenomenon where the resulting wave has a higher amplitude, than the interfering waves. Destructive interference is a phenomenon where the resulting wave has a lower amplitude, than the interfering waves. In another embodiment, reflection of a wave is defined as what has been there and what could have been there. Refraction, diffraction and absorption are interrogating the nature of knowing in the context of the constitutive conditions of being. Polarization is distortion over constrains of the environment and interference displays combined effects of waves. Thus, the information of the physical and chemical nature of the surrounding environment 118 and the target system 117 are contained in the wave behavior and propagation of the wave in time and space. The OOIS 100 learns and extracts information of the wave behavior and propagation of the wave in time and space and applies the strategic FP to sustain the vitality of the target system 117.

Figure 2:
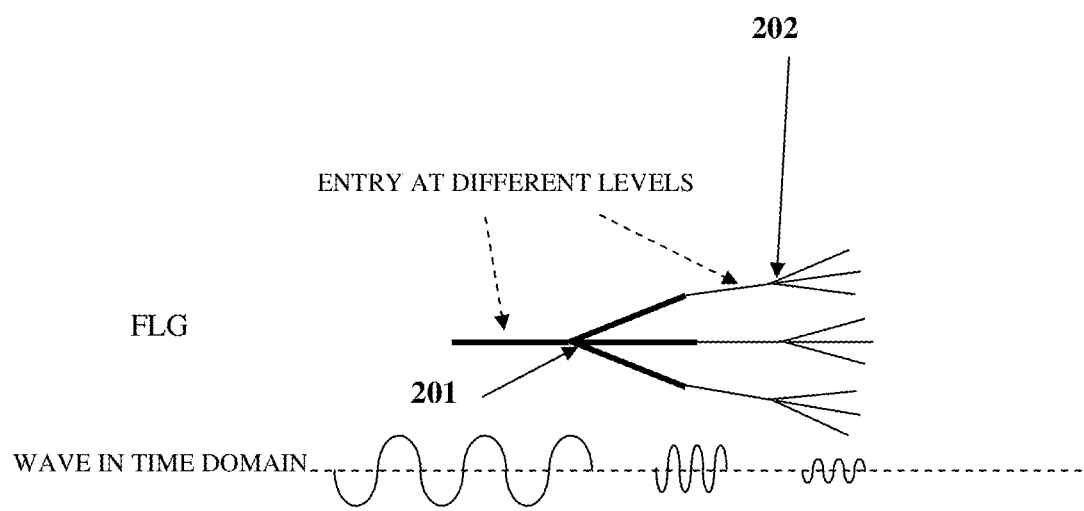
FIG. 2 exemplarily illustrates fractal like geometry structures of a tree structure and a wave.

The wave is magnified by logical rules of a fractal like geometry (FLG) structure. FIG. 2 exemplarily illustrates fractal like geometry structures of a tree structure and a wave. A fractal is a non-regular geometric shape that has the same degree of non-regularity on all scales. In an embodiment, fractals are described as never-ending patterns. Examples of FLG structure comprise a tree structure, a fern leaf structure, etc. The logical rules of FLG structure comprise self-similarity and non-integer dimension. Self-similarity of a FLG structure refers to the fact that on each magnification step 201 and 202 of a FLG structure, the FLG structure shows the same shape, which is characteristic of that particular FLG structure. As illustrated in FIG. 2, the structure in the magnification step 201 is similar to the structure in the magnification step 202. Further, a fractal has a fractional dimension. Generally, a point in space has a dimension of 0, a line in space has a dimension of 1, and a plane in space has a dimension of 2. However, a fractal has a dimension which is expressed in terms of a fraction. A curve is an example of a fractal. The boundary of the curve is very, very intricate and has a dimension between 1 and 2 but closer to 2, i.e., a fractional dimension. It is possible to describe and interpret most wave behaviors in fractal geometry, where the waves propagate into different frequency regions. FIG. 2 exemplarily illustrates the fractal like geometry structures of waves represented in time domain that travel into fractal branches and change their frequencies. The waves generated and received in different parts of the target system 117 can be converted into waves at common frequency by transmitting through fractal like geometries in the OOIS 110 system.

The waves at common frequency can resonated and the object oriented information system (OOIS) 110 can spontaneously recognize the strongest dominating rhythms as the FP of the target system 117 that is intrinsic to the moment and can be altered by future events. It will become a new point that will cause changes to the entire target system 117. The FP comes from all the waves in the surrounding environment 118 and the target system 117 and represents game planning in the target system 117. If the FP i.e., strongest resonating wave in the target system 117 is in harmony with all the waves inside the target system 117, the FP is said to be favorable. If the FP is not in harmony with all the waves inside the target system 117, the FP is said to be unfavorable. The central storage in time (CST) 106 watches information from each level, and picks out those signals i.e., the information wave packets from the sensory units 111. The information wave packets comprise information of the surrounding environment of the target system and the information within the target system 117 that are abnormal and projected in the time domain. In cases of conflicting interests between different time durations, such as short term goal verse long term goals, the OOIS 100 chooses the FP that fits the long term goal favorable for the vitality of the target system 117. If there are multiple uncontrollable factors, the OOIS 100 decides based on the best possibility of the time and place of the target system 117, and reassesses the situation at each time of the steps. If the accumulative steps that are to be performed by the motor unit 119, for moving the target system 117, need an alternative that comprises unfavorable initial steps, the central storage in space unit (CSS) 108 stores those situations and chooses the steps that may be unfavorable in the beginning but offers a better overall outcome. For example, a clear intention to reach an object is accumulative steps to achieve the object in three dimensional space until the objective is reached.

The sensory units such as the tactile unit 111a, the visual unit 111b, and the audio unit 111c work in different ways that provide the object oriented information system (OOIS) 100 a different perspective in the internal and external aspect for the target system 117. The sensory units 111 perceive their three dimensional surrounding comprising layers (102, 105, 110, 115, and 118 respectively) and scales or dimensions of objects within and outside the target system 117 in the time domain. The visual unit 111b that obtains information beyond the visual light spectrum, i.e., in frequencies above and below the visual spectrum, gives the OOIS 100 the three dimensional information and the scales or dimensions of the object via the "color" of the object. The audio unit 111c provides the OOIS 100 the time domain plus layers that are not detectable by the visual unit 111b, such as objects that are hidden behind visual obstacles, but detectable via an audio signal, for example the rhythmic audio wave, that can travel behind the visual obstacles. The tactile unit 111a provides the OOIS 100 with information of the objects within the target system 117 and objects external to the target system 117 that are in close proximity to the target system 117. The tactile unit 111a also provides the physical property such as the texture of the objects that are within the target system 117 and the objects external to the target system 117. The visual unit 111b also detects chemicals, and small particles that diffract the chemical composition and size of the particles. The size of the particles range from a small size particle in the air, including vapors, to large droplets comprising large molecules. Visual objects are exact, concrete, and multidimensional, while audio objects are transient one dimensional and less concrete. Each of the sensory units 111 combined offer a complete set of information within the target system 117 and outside the target system 117.

The visual unit 111b senses waves, for example, electromagnetic waves, in the visual region along with electromagnetic waves in the microwave, infrared, ultraviolet and partially in the X-ray region. The visual unit 111b can utilize passive visual inputs and does not need active illumination for visual detection; however, the visual unit 111b can use active illumination for interacting with the surrounding 118. Visual inputs are concrete in space and can be transmitted in specific directions in real space to spatial mapping in virtual space in the dynamical mapping matrix system (DMM) 104, the layered mapping system in time (LMST) 107, and the layered mapping system in space (LMSS) 109 developed by the object oriented information system (OOIS) 100 and are stored in layers in correlation with time domain. In an embodiment, the OOIS 100 comprises multiple audio detectors (not shown) located in the OOIS 100. The audio sensory inputs start from external audio detectors, for example, the audio unit 111c, for obtaining information surrounding the audio detectors at multiple locations and merge with audio detectors from the four layers in the OOIS 100, i.e., the inner core 102, the outer core 105, the inner shell 110, and the outer shell 115. The information enters the DCC 103 at each respective level to resonate with each other and pass information to the CST 106, and further over to the CSS 108. Audio waves comprise mechanical information of the material such as fatigue of broken parts. An abnormal audio signal can provide the information about the size and shape of parts that are broken, therefore helping to diagnose mechanical failure of the OOIS 100. The audio wave also provides clues of objects that are hidden behind solid objects that can be considered when obstacles block the visual unit 111b. The sensory units 111 such as the tactile unit 111a, the visual unit 111b, and the audio unit 111c have one or more mini motor units (MMU) 111d that help to adjust the direction and position of the sensory units 111 instead of the entire OOIS 100 or the target system 117. The audio unit 111c detects the audio waves and also produces audio waves to interact with the surrounding environment 118. The frequencies of the audio unit 111c expand beyond human audible threshold from low infrasonic region, i.e., less than 20 Hz to ultra-sonic, i.e., above 20 KHz. In an embodiment, the audio unit 111c sensing overlaps with the tactile unit 111a sensing that mainly senses the tactile and contacting force to the surrounding 118.

In the system shown in FIG. 1, there two types of connection between units, one for power transfer (PT), and one for information transfer (IT). Power transfer occurs through power transfer (PT) channels, and information transfer occurs through information transfer (IT) channels. The PT channels are thicker in diameter and limited in numbers. The IT channels are thinner wires and numerous and throughout in OOIS 100. Each unit comprises a mechanism to run itself in the required rhythms and the OOIS 100 can modulate the functions of the units of the object oriented information system (OOIS) 100. Input from the DCC 103 can either tone up or tone down the activities in other units including the rhythmic power unit (RPU) 101. The IT connections can translate waves from higher levels in the DCC 103, the CST 106, or the CSS 108 to local levels in units for facilitating OOIS 100 for providing better control over the overall activities of the OOIS 100 and/or the target system 117.

Figure 14A:
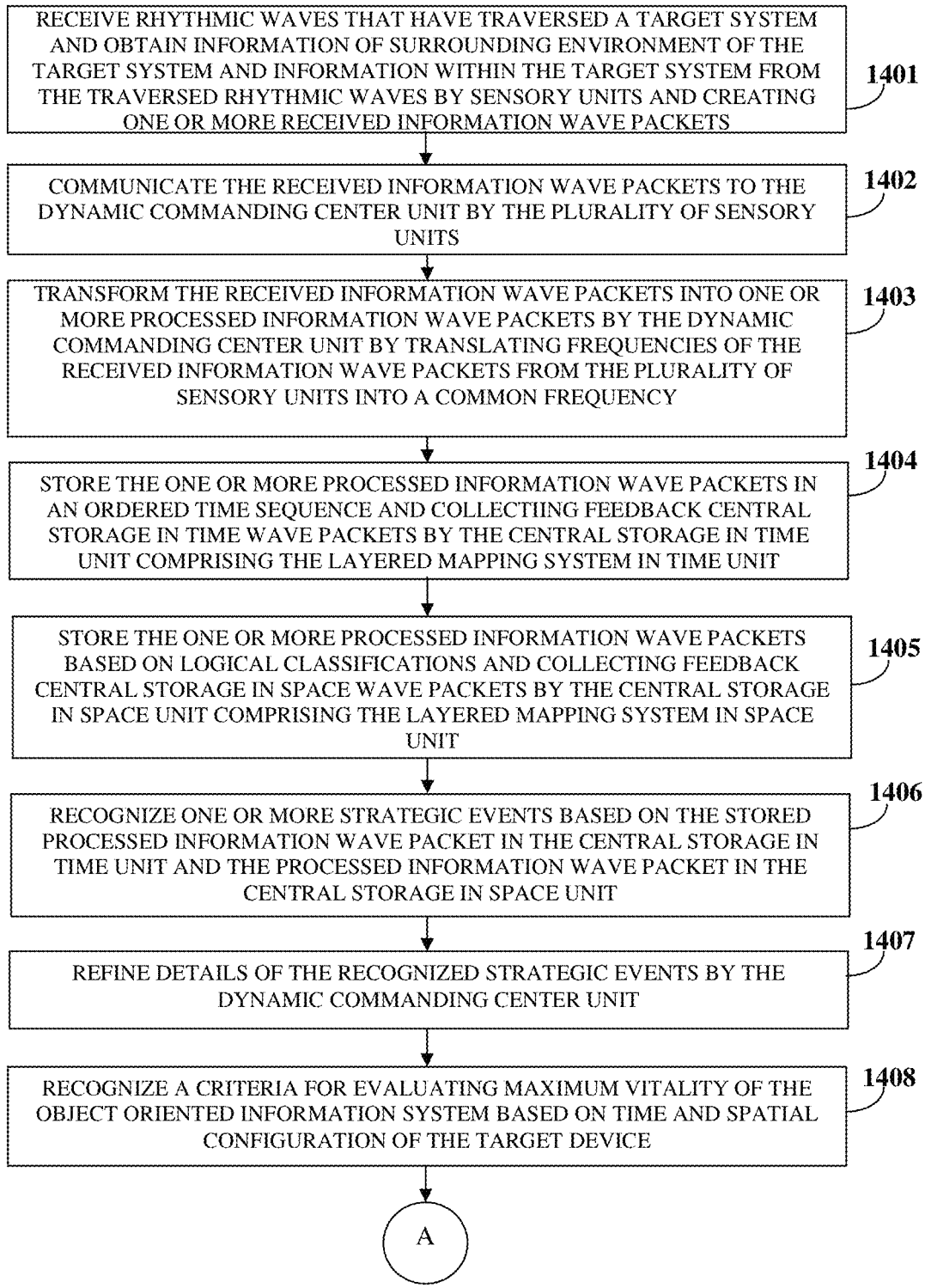
FIGS. 14A and 14B illustrate a method for monitoring and sustaining the vitality of a target system dynamically.
Figure 14B:
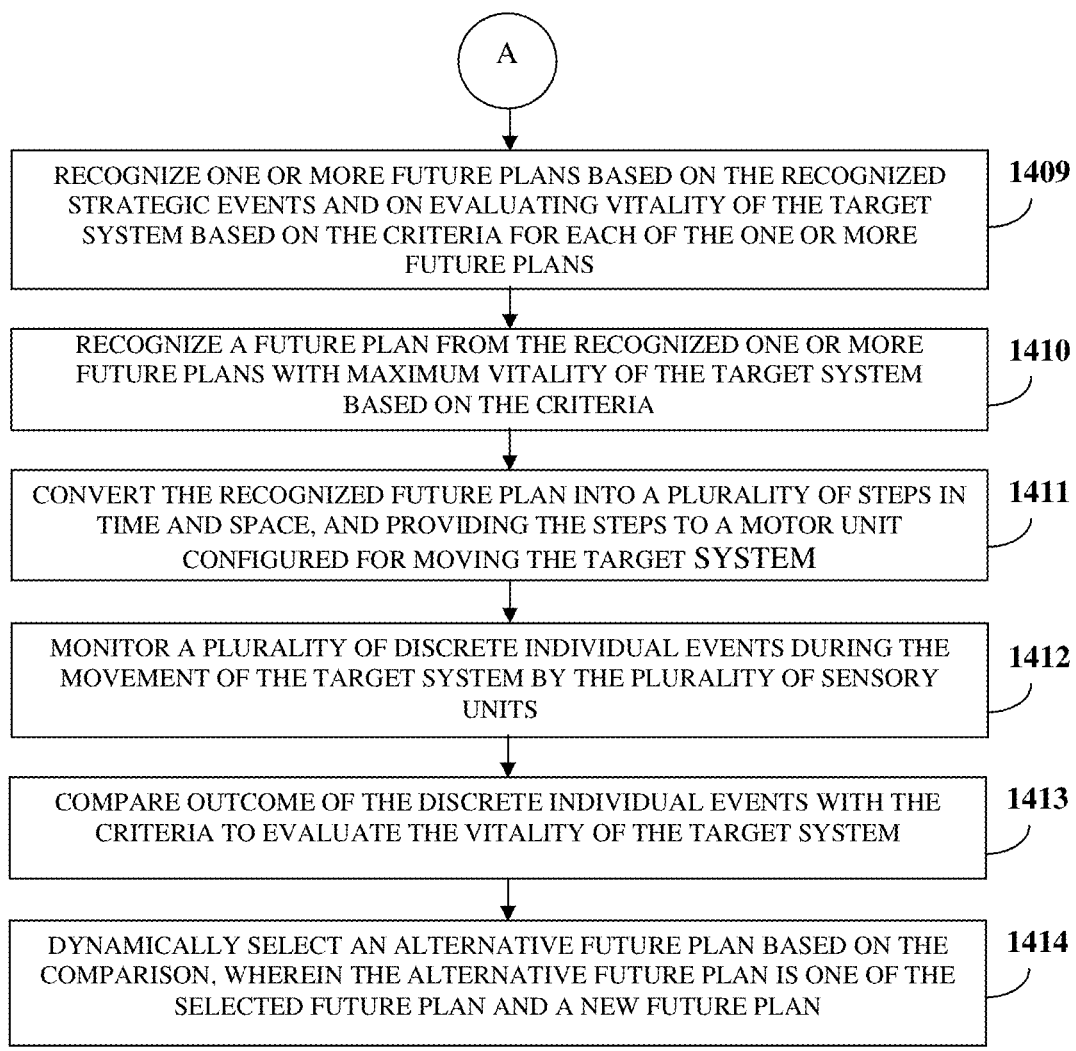

FIGS. 14A and 14B exemplarily illustrate a method for monitoring and sustaining the vitality of the target system 117 dynamically comprises providing the object oriented information system (OOIS) 100 for the target system 117. The OOIS 100 is installed inside the target system 117. In an embodiment, the OOIS 100 is installed on an outer surface of the target system 117. In another embodiment, the OOIS 100 is located remotely from the target system 117 with the sensory units 111, motor unit 119 and the RPU 101 located in the target system 117. The remotely located OOIS 100 also comprises an RPU 101. The RPU 101 transmits rhythmic waves within the target system 117. The method comprises receiving 1401 the rhythmic waves that have traversed the target system 117 and obtaining information of the surrounding environment 118 of the target system 117 and the information within the target system 117 from the traversed rhythmic waves by the sensory units 111. The sensory units 111 create one or more received information wave packets using information of the surrounding environment 118 of the target system 117 and the information within the target system 117. In an embodiment, the one or more received information wave packets are obtained by transforming information of the surrounding environment 118 of the target system 117 and the information within the target system 117. The sensory units 111 also monitor the target system 117 using the received information of the surrounding environment of the target system 117 and the information within the target system 117.

The method further comprises communicating 1402 the received information wave packets to the DCC 103 by the sensory units 111. The method further comprises transforming 1403 the received information wave packets into one or more processed information wave packets by the DCC 103 by translating frequencies of the received information wave packets into common frequency. The method further comprises storing 1404 the one or more processed information wave packets in an ordered time sequence and collecting feedback central storage in time wave packets by the CSS 108 comprising the LMSS 109. The method further comprises storing 1405 the one or more processed information wave packets based on logical classifications and collecting feedback central storage in space wave packets by the CST 106 comprising the LMST 107. The method further comprises recognizing 1406 one or more strategic events based on the stored processed information wave packet in the CST 106 and the processed information wave packet in the CSS 108. The method further comprises refining 1407 details of the one or more strategic events by the DCC 103. The method further comprises recognizing 1408 a criteria for evaluating maximum vitality of the target system 117 based on time and spatial configuration of the target system 117. The method further comprises recognizing 1409 one or more future plans based on the recognized strategic events and on evaluating the vitality of the target system 117 based on the criteria for each of the one or more future plans. The method further comprises recognizing 1410 a future plan from the recognized one or more future plans with maximum vitality of the target system 107 based on the criteria.

The method further comprises converting 1411 the recognized future plan into multiple steps in time and space and providing the steps to a motor unit 119 configured for moving the target system 117. The method further comprises monitoring 1412 discrete individual events by the sensory units 111 during the movement of the target system 117. The method further comprises comparing 1413 outcome of the discrete individual events with the criteria to evaluate the vitality of the target system 117. The method further comprises dynamically selecting 1414 an alternative future plan based on the comparison. The alternative future plan is either the selected future plan or a new future plan. The DCC 103 translates the feedback central storage in time wave packets from the central storage in time unit (CST) 106 to a single frequency.

The OOIS 100 comprises the rhythmic power unit (RPU) 101 for supplying rhythmic power to units of the OOIS 100. The RPU 101 maintains the sustainability of the OOIS 100 in the time domain by producing repetitive rhythmic power over the entire vital cycle (VC) of the OOIS 100. The RPU 101 is designed based on forms and rhythms of energy sources from the surrounding environment 118 of the target system 117 and the OOIS 100. The OOIS 100 develops its activities based on the rhythm. Each unit, such as the RPU 101, the DCC 103, the CST 106, and the CSS 108, have different intrinsic rhythms (IRs) as the activities of the RPU 101, the DCC 103, the CST 106, and the CSS 108 are dynamic events that effect themselves and the OOIS 100. The WPs from each unit, that is, the RPU 101, the DCC 103, the CST 106, and the CSS 108 exhibit complex wave forms in time domain and have different IRs that is intrinsic to each unit. Each unit, that is, the RPU 101, the DCC 103, the CST 106, and the CSS 108, have a dedicated surrounding and internal space that defines confinement of the waves evolving in and evolving from each unit. The waves propagate to the boundary of the confinement and bounces back in completion of the IR cycle. The physical conditions of the boundary such as material, shape, design as well as the activities of the unit are determining factors of the IR of each unit, that is, the RPU 101, the DCC 103, the CST 106, and the CSS 108. Each information transfer channel (IT) 124 of the sensory units, that is, the tactile unit 111a, the visual unit 111b, and the audio unit 111c continuously produce chains of rhythmic information. The motor unit (MU) 119 produces active movements and timely information as the motion of the MU 119 produces new information at each time interval thereby changing the IR of the MU 119. The WP and IR from the units i.e., the RPU 101, the DCC 103, the CST 106, the CSS 108, the tactile unit 111a, the visual unit 111b, the audio unit 111c, the MU 119 differ significantly from each other, and the collection of IRs and WPs of the units contain the information of the device in the time domain, which provides a package of information to maximize the vitality.

The wave packets (WPs) propagate through the entire time and space domain through layers of objects and space and register traces in the dynamic commanding center (DCC) 103, the central storage in time (CST) 106, and the central storage in space (CSS) 108. Random exploration of expanding waves in time domain provides the object oriented information system (OOIS) 100 maximum occupancy of time and space. Extension of exploration into time domain offer possible outcomes in future that may or may not maximize the vitality of the target system 117 or the object oriented information system (OOIS) 100. The OOIS 100 resonates the future plans (FP) that offers best vitality for the entire vital cycle (VC). Although the waves exhibit continuous cycles in the time domain, upon observation in the direction of each wave and integration over time, each cycle and the WP of cycles behave as individual events such as particles. OOIS 100 converts the FP into steps of actions, for example, movements produced by the motor unit 119 while the sensory units 111 monitor outcome of discrete individual events. If the outcome of the FP fulfills the criteria of maximizing the vitality for the target system 117 or the OOIS 100, the OOIS 100 continues forward, else the OOIS 100 creates a new FP with better outcome based on new information.

The intrinsic rhythms (IRs) of wave packets (WPs) of each unit that are different form each other and layers of the OOIS 100 connect, communicate and interact with each other to integrate for generating future plan (FP) for the entire target system 117 and/or the OOIS 100 and for evaluating the outcome. The waves use resonance, in which a significant amount of energy transfers from one state to the other, for interacting with each other. The successful energy transfers require rhythm and phase matching. The resonance and the energy transfer between two wave forms are known in nature in both classical and quantum mechanics, such as celestial mechanics, mechanical resonance, acoustic resonance, electromagnetic resonance, nuclear magnetic resonance, electron spin resonance and resonance between quantum states and wave functions. For example, electrical resonance occurs in an electric circuit at a particular resonant frequency when the impedance of the circuit is at a minimum in a series circuit or at maximum in a parallel circuit. The resonance in circuits is used for both transmitting and receiving wireless communications such as television, cell phones and radio. Coherent resonance occurs when the rhythms are the same value and/or when the rhythms are exact integer multiple or divisions. The coherent resonance is called a high order resonance (HOR). A scale-up HOR is when a new rhythm is a multiple of an original rhythm, and a scale-down HOR is when the new rhythm is an exact division of the original rhythm. The scale-up HOR connects higher rhythms with lower rhythms. The scale-down HOR connects lower rhythms with higher rhythms. The HOR occurs between parts that are different scales and sizes in which the frequencies are in exact multiples or divisions. For example, a group of 3 parts with common rhythms are 3 times slower than one part. Enhancement from the HOR coherence resonance is much less than the same value resonance due to natural fading of the waves, however significantly higher than those not in coherence or in chaos. Through the HOR, a unit smaller in size and scale resonates with units larger in size and scale, thus the units or parts inside OOIS 100 and/or the target system 117, and the surroundings interact in time domain via the HOR. For example, in celestial mechanics, an orbital resonance occurs when two orbiting bodies exert a regular, periodic gravitational influence on each other, usually due to their orbital periods being related by a ratio of two small integers. Orbital resonance enhance the mutual gravitational influence of the bodies, which results in an unstable interaction, in which the bodies exchange momentum and shift orbits until the resonance no longer exists. Under some circumstances, a resonant system can be stable and self-correcting, so that the bodies remain in resonance. Examples are the 1:2:4 resonance of Jupiter's moons Ganymede, Europa, and Io, and the 2:3 resonance between Pluto and Neptune.

The units in the OOIS 100 do not share a common frequency in which the layers of the OOIS 100 interact with each other. The OOIS 100 uses high order resonance (HOR) to bring the inputs from units of the OOIS 100 to the common frequency. However, if the surrounding changes, the OOIS 100 redesigns activities to adapt to a new rhythm. The averaged value of the rhythm is determined by size of the OOIS 100 or the target system 117, units of the OOIS 100 and the surrounding 118 to match the changing pace of the OOIS 100 or the target system 117 with the surrounding 118. For example, in an embodiment, for a device having a size of one meter, the time duration will be one second to make changes in its position in a typical activity. The time duration also depends on the natural cycle in the surroundings 118. In a natural setting on earth environment, days, weeks, and months of variation are typical periods used.

Measurement in time is a scalar: from 1 and up, building up the space and dimension of time. The continuous rhythms of the RPU 101 divide the vital cycle (VC) of the target system 117 in the time domain into small segments. Thus, the status of the OOIS 100 or the target system 117 in time domain during the entire VC of the OOIS 100 or the target system 117 becomes predictable in the scalar field in the OOIS 100.

During the vital cycle (VC) in the time domain, the rhythm of the rhythmic power unit (RPU) 101 naturally exists as a range of spontaneous variation from an average value, drifting up and down, but the rhythm remains fairly stable and independent from other parts of the device. As the rhythmic waves transverse the units of the target system 117, other parts or units of the target system 117 and/or OOIS 100, receive the rhythmic power. The units of the target system 117 and/or OOIS 100 absorb the rhythms and pass different rhythms to next part or unit. The continuing waves originating from the RPU 101 and propagating to other parts or units of the target system 117 produce a common wave effect such as interference, resonance, coherence, bifurcation, and chaos. The changing rhythms of waves from RPU 101 interact with waves spread over the target system 117 and bounce backward, as the functionality of the target system 117 fluctuates between chaotic states to resonated coherence. Abnormal states cause severe disturbances to the target system 117 and result in malfunction, or even reset of the rhythms of various part or units of the target system 117 including the RPU 101. Thus, a periodical reset of the target system 117 is required to maintain the functionality of the target system 117.

Contrary to the rhythms that bring disturbances to the target system 117, there are rhythms from the RPU 101 that bring coherence to the target system 117. The RPU 101 rhythms that are the same or its multiples or exact divisions with other waves can resonate with each other, forming an enhanced coherence effect to the vitality of the device. The enhanced resonance of the RPU 101 with coherent parts or units of the target system 117 and surrounding 118 is recognized by OOIS 110 and unite the target system 117 and the surrounding 118 and enhances the functionality of the target system 117. The state of resonated coherence has a stronger energy state than others states. If the OOIS 100 is designed to use the extra energy in the resonated coherence of the target system 117 to further sustain and enhance the resonant coherence, the vitality of the target system 117 sustains over a longer period of time. This gained sustainability occurs in an objective and natural variation of the RPU 101 rhythms without external interventions and commands, and can further prolong the sustainability, and form a positive cycle of sustained vitality via OOIS 100 inside the target system 117. The positive coherent effect eventually fades away as the rhythms phase out from each other and other parts drift away from the resonating frequency. This positive coherence from the RPU 101 is recorded in the OOIS 100 and incorporated in the vitality planning of the target system 117 in the future. A new coherence may occur again in the future from the natural variation of the rhythms from the RPU 101 and starts a new rhythm that unites parts or units of the target system 117 and improves the adaptation of the target system 117 with the surrounding 118.

The variations of the rhythmic power unit (RPU) 101 reflect the status of the RPU 101. In order to integrate within the target system 117 and with the surrounding 118, the OOIS 100 has to monitor the units inside and in the surroundings of the units via sensory units such as the audio unit 111*c* (wave in the air via molecules), the visual unit 111*b* (electromagnetic waves via space), and tactile unit 111*a* (mechanical impacts via solid surface). The rhythmic waves from the RPU 101 spread to other parts or units of the target system 117 and at the same time to the surrounding of the units over three dimensional space in the target system 117, thus producing audio, visual and mechanical interaction signals that are detected by the sensory units, and forwarded to the dynamic commanding center (DCC) 103 in the outer core 105 of the OOIS 100 with the dynamical mapping matrix system (DMM) 104 that maps timely progression of the rhythms in the target system 117. The DMM 104 is the information architect for the fractal like geometry (FLG) structures in the DCC 103 with sensory waves entering the FLG structures at the matching levels. The waves converge inside the DCC 103 into a compacted form of the wave packets (WP), which are then forwarded to the central storage in time (CST) 106 in the inner shell 110 of the OOIS 100 to a system called layered mapping system in time (LMST) 107. The time domain is integrated over logical dimensions and registered in time less system in central storage in space (CSS) 108 in the inner shell 110 of the OOIS 100 with the LMSS 109. Here, time less system refers to the fact that the CSS stores the inputs in a spatial configuration. The logical dimensions are new spatial dimensions created by the OOIS 100 based on the space created by the waves, which may not be same as the visual space perceived by a human.

The density of information in time domain varies if the motor unit (MU) 119 is at work. The MU 119 changes the geometry of the target system 117 continuously, and the sensory units continuously accumulate information in small time increments. The smaller the time increments, the more the amount of information grows exponentially with time, and the OOIS 100 may be unable to update simultaneous occurring events, whereas use of a dynamical mapping matrix system (DMM) 104 facilitates integration of past event with the current event by storing information in the central commanding center (DCC) 103 thereby not increasing the amount of information with time. The repetitive events with minimal changes to past events are designed to be overwritten and omitted, and non-repetitive events that are notably different are stored in the DMM 104 of the DCC 103. Therefore, the OOIS 100 can manage to maintain the amount of information stored in the DCC 103. As explained above, the DCC 103 has fractal like geometry (FLG) structures that translate the information into the same frequencies. The FLG structures in DCC 103 are built and developed over multiple events and over a long period, and the FLG structures reflect the style and type of the target system 117. A developed FLG can process a large amount of information in vectorized and parallel ways rapidly, in a small amount of time. In vectorization and parallelization, waves are repackaged in matrices with the inherence properties of the wave that can be processed and computed simultaneously. The information processed in the DCC 103 are thus concentrated, refined and fine-tuned to reflect the current status of the target system 117 and then passed over to next step or unit of the OOIS 100. The DCC 103 is renewed continuously to reflect continuous changes in the target system 117.

The information in the DCC 103 is updated continuously, and significant events are passed over to the LMST 107 in the CST 106 in an orderly time sequence. Since the events occur naturally in the time domain, and even though the events are converged in the DCC 103, the events naturally retain their timely position in time domain. Therefore. as the events are stored, the events come in a natural time sequence in the LMST 107. The LMST 107 differs in time domain and spatial domain. The LMST 107 comprises a matrix. The LMST 107 matrix has orders in the time domain and columns in the spatial domain. The LMST matrix is transformed from but different from the DCC 103 matrix. The information is further condensed in the CST 106 by integrating over the time domain. The repeating and insignificant events in the spatial domain are further designed to be omitted and significant events in the spatial domains are stored in the LMSS 109 in the CSS 108 summarized in spatial and logical orders. The LMST 107 is labeled by the time, spatial clues of the events and layers of the different size of the device and environment or surrounding of the device are labeled accordingly in the LMSS 109. The chaotic events are omitted and the events that cause resonating coherence of the units in the OOIS 110 are stored in the LMST 107 and the event of significance is evaluated in the target system 117.

The RPU 101 supplies rhythmic power to the units of the OOIS 100. The object oriented information system (OOIS) 100 modulates the rhythm of the RPU 101. The OOIS 100 information from the DMM 104, the LMST 107, and the LMSS 109 are reduced from multidimensional, multifactor and multi-layered to a single dimensional single converging points (SCPs) in the time domain. Instead of remaining at a single fixed value, the rhythm of the RPU 101 fluctuates around preset average value, and scans over the rhythms in time domain. Thus, the information in the OOIS 100 converges into one dimensional modulation in time domain to the RPU 101 and the information is transmitted to the units of the OOIS 100. The OOIS 100 provides new updated rhythms to the units of the OOIS 100 that change the status of the target system 117 to a better status, to maintain vitality. The incremental changes accumulate in trajectories in time domain and in space. The wave form of rhythmic power from the RPU 101 is not just a simple spike. Instead, the wave form of rhythmic power from the RPU 101 comprises multiple phases that in time domain follow the simulating of the target system 117. Each spike in the wave form of rhythmic power from the RPU 101 works for the better interaction with units in the target system 117, and the variation between the phases of each spike work as variables to maximize the vitality. OOIS 100 modifies the rhythms and the phases of spikes within the rhythms, the phase for each spike and the time duration between spike to maximize the outcome. The structures, variables, and the geometries that are built in time domain are sophisticated to interact with units of the target system 117 and the OOIS 100 builds three dimensional multi-layer structures for the target system 117. In an embodiment, in time domain, the OOIS 100 interacts with the inputs, i.e., information wave packets corresponding to units in the target system 117, which become part of the OOIS 100 and thus evolve differently within the OOIS 100. Compared to inputs, i.e., information wave packets corresponding to units in the target system 117 in real world, the information wave packets corresponding to units in the target system 117, which have already become part of the OOIS 100 produce different results which is analyzed by OOIS 100.

Each unit of the OOIS 100 has a functional lifetime even though they received same rhythmic power from the rhythmic power unit (RPU) 101 and modulates original rhythms to adapt to the functions performed. The RPU 101 rhythms are modulated so that the rhythms of units match and work together. If the object oriented information system (OOIS) 100 decides that the RPU 101 rhythms need to slow down, the entire target system 117 will slow down to adjust the units, and falls into a slow and "painful" period in which the entire target system 117 is adjusted and every unit in the OOIS 100 adjusts the target system 117 to a new status. If the OOIS 100 decides that the RPU 101 rhythms need to speed up, the units of the target system 117 speed up and less information needs to be incorporated into the target system 117. Therefore, the target system 117 shifts into a fast or "delighted" period. Thus, the OOIS 100 constantly undergoes events of wave packets (WP) in either slow or fast periods to adjust internal or external changes. Each event unites units of the target system 117 together, the larger events, such as the motor unit (MU) 119 involvement, the larger is the step the OOIS 100 has to take to improve the vitality. The periods of slowing and speeding events are recorded in the central storage in time (CST) 106 and evaluated in the central storage in space (CSS) 108 and are labeled as ideal internal and external factors and time scales. In the future, if needed, the OOIS 100 matches external condition with internal condition and time scales and intentionally triggers the slowing and the speeding to maximize the vitality. If needed, the OOIS 100 also designs internal factors to avoid a slowing process which decreases the vitality.

The level of activity for the target system 117 is determined based on the natural rhythm of the surrounding, the rhythm of the target partner such as human, strategic planning from the object oriented information system (OOIS) 100 in the central storage in space (CSS) 108 and the central storage in time (CST) 106, and the internal responses from inside the target system 117 for sorting information or for conservation of energy. The level of activities may range from reactions in milliseconds to hibernation in days and weeks or even months. Higher level in the information chain, from the rhythmic power unit (RPU) 101 to the dynamic commanding center (DCC) 103, the CST 106, and the CSS 108, relates to faster rhythms. For example, the frequency range from below 0.1 Hz relates to deep hibernation, 1.0 Hz relates to basic activity, 5.0 Hz relates to basic sensory, 10 Hz relates to high level sensory, 15 Hz relates to active fast MU actions, 20 Hz relates to CST 106, and 40-80 Hz or higher relates to CSS 108 for large amount of data processing and attentiveness. To activate a higher level of resonance, the OOIS 100 requires the high order resonance (HOR) in the fractal like geometry (FLG) structures in the DCC 103, and in wave propagations in the CST 106 and the CSS 108, with correct rhythm and phase like ignition of a fire. Here, a fire ignition is an example of a fractal like structure where a chain reaction occurs from small to large scale similar to a fractal tree in time domain. The HOR happens in steps of parallel clusters of fractal like self-organizing crystallization much like the solid state physics dynamic process where crystals builds themselves up in fractal structure in a saturated solution when the CSS 108 and the CST 106 are saturated with waves ready for the HOR. The HOR forms rapidly when there are many waves saturated in space and time. The self-organizing and parallel clusters are combined from microscopic size to bigger sizes without losing content of the clusters. The continuous chain of the HOR that connects the DCC 103 and the CST 106 creates a temporal series of a river of flowing waves and their ripples. The sensory information such as sound, light, and touch add into the "river", bring parts of the target system 117 or the units of the OOIS 100 together in the confined space to form a saturated space. As the signals scanning around the resonating frequencies via the DCC 103, and at a critical point, may trigger a "fire" or future plan (FP), and a fractal process clustered around a new nucleus from the variations of the RPU 101 rhythms and transit to a higher state with a cascade release of energy of the waves that were trapped and found tunneling via the HOR. The waves from the firing spread through the target system 117 for redefining the state of the target system 117.

Though the object oriented information system (OOIS) 100 from the central storage in time (CST) 106 and the central storage in space (CSS) 108 constraints the rest of the units in the target system 117, the unity of the rhythmic power unit (RPU) 101 with the rest of the units in the OOIS 100 maintains vitality of the target system 117. The process from the RPU 101 to the dynamic commanding center (DCC) 103 to the central storage in time (CST) 106 and the central storage in space (CSS) 108 is a gradual step, from a small region of the unit, to larger areas at each step. At the hibernation stage, the DCC 103, the CST 106 and the CSS 108 are minimal activities whereas other units of the OOIS 100 work with a time clock on the RPU 102 that is running at a very low rhythm. The OOIS 100 utilizes the hibernation time to reprocess the information received during the active periods in the CST 106 and the CSS 108. The OOIS 100 groups the information obtained into clusters and into small modules, and information with lesser importance and repetitive information are transformed into forms that are not complicated. In an embodiment, at a basic stage, the DCC 100, the CST 106, and the CSS 108 are less active and less organized and coordinated, thus the DCC 100, the CST 106, and the CSS 108 may independently process their own contents in clustering and paralleling to remove bug and clumps that are not in harmony in the high order resonance (HOR) process. In order to be alert to visual and audio changes to the surroundings 118 or the environment, a periodic signal is sent to the visual unit 112 and the audio unit 113 to maintain basic sensory. As the information in the CST 106 and the CSS 108 are transformed into clearer zone, the CST 106, and the CSS 108 will process the information in longer time and further depth. The motor unit (MU) 119 portion of the OOIS 100 has electrical and mechanical parts that comprise different rhythms and reaction time compared to the OOIS 100. The mechanical parts require physical structures, and the mechanical parts build fatigue that result in different rhythms. The mechanical parts require oil to lubricate and connect to each other. The mechanical parts also require periodical calibration. The rhythms for the mechanical parts are lower than the rhythms for the electrical parts.

The DCC 103 and the dynamical mapping matrix system (DMM) 104 are dynamic targeting and interaction matrix center for the RPU 101, the sensory units such as the tactile unit 111, the visual unit 112, the audio unit 113, the CST 106, and the CSS 108. The other function of the DCC 103 is a rapid responding system (RRS), where the DCC 103 rapidly responds to the timely changes in the target system 117 based on the past information from the CST 106 and/or the CSS 108, considering the current information from the RPU 101. The DCC 103 reflects the interaction between the past rapid response strategies from the CST 106 and/or the CSS 108 and the current situation from the RPU 101 that carries the present trait of the CST 106 and/or the CSS 108 of the OOIS 100. The wakening process requires sequential activation of units in the OOIS 100 to update new information from the DCC 103 dictated by the RPU 101 that is different from the previous system in the CST 106 and/or the CSS 108, since the RPU 101 may deliver a new rhythm. Although the DCC 103 does not comprise the depth and broadness details from updating process of the CST 106 and/or the CSS 108, the DCC 103 reflects current new situation and rapidly addresses the timely changes in the target system 117, thereby improving the vitality. This mechanism supervises the present setting from the CST 106 and/or the CSS 108 and occasionally produces a different prediction from what the CST 106 and/or the CSS 108 has predicted, and changes the present path of the CST 106 and/or the CSS 108. This divergent information gathering and converged decision making process is rapid, and in an embodiment, omits trivial details that are repetitive and have little effect on the vitality of the target system 117. The correction of details occurs after the events are updated in the CST 106 and/or the CSS 108.

Mini motor units (MMU) 111*d* of the sensory units 111 adjust the direction and position of the sensory units 111. In an embodiment, the MMU 111*d* also uses rapid movement (RM) to adjust the direction and position of an entire sensory unit 111 or a single part of the sensory unit 111 that are designated to the MMU 111*d*. This allows the sensory unit 111 to scan over small steps in time and space. RM creates small random samples that form a cloud of data over the space differing at each time, and allows waves to expand and evolve, and create a sense of "at will", because the waves can grow within the inner space, unaltered by outside factors. The RM creates an additional space and dimension to let waves from the RPU 101 to expand and take off. The RM of the detection device can sense the space and time around its current spatial location, and the waves can feel and resonate with the incoming waves. The RM sets the RPU 101 free in an open space and allows the object oriented information system (OOIS) 100 to follow the main rhythm from the RPU 101 to detect the open space, and to conceive the best FP to maintain and improve the vitality of the target system 117.

Due to the wave natural of the device, rhythmic power source such as alternating current, and wireless charging via electromagnetic interaction are used by the OOIS 100. Inverters can be used to convert direct current into alternating current. The OOIS 100 detects the energy source via visual electromagnetic at a wide range of frequencies, and the motor unit (MU) 119 moves the target system 117 to the appropriate location and arranges to complete the charging process. The pulsed electrical energy can be easily obtained and stored. The information stored inside the OOIS 100 are upgraded and transmitted via the wireless technology. Electrical energy can also be obtained via solar panels or more effective via long distance electromagnetic charging technology. The sensory detection of visual and audio signals facilitate in analyzing potential insult to the object. Chemical sensor for larger and small particles including water is obtained via specialized sensory units. In order to conserve the energy, the OOIS 100 systematically turns off units that are not in use, and maintains the right level of activities during each time instance.

FIG. 2 exemplarily illustrates a fractal like geometry (FLG) structure. The high order resonance (HOR) scales-up or scales-down via spatial geometry. The FLG structures and self-organizing structures are recognized widely in spatial geometries. The FLG structures can relate higher scales to lower scales and vice versa, thus the FLG structure provides means to allow waves from high scales to be translated and to communicate with waves from lower scales, and vice versa. Resonance via spatial geometry can be established with physical structures, which is faster, modular, and predictable. The HOR can occur also naturally in time domain. The FLG structures are well recognized in spatial geometries, but not as much in time domains because of the difficulty to measure rapid, transient nature of time. In several cases, the FLG structures are viewed as turbulence, chaos, or tunneling effect. Fractal in time domain can instantaneously trigger events similar to FLG structures in scalar field. Since each wave packet (WP) has a different course of propagation, the OOIS 100 treats each WP as a subset of objective event that completes in its own vital cycle (VC), leaving latent cues in time domain and patterns in space. The FLG structures in both space and time domain offer windows for waves from high scales to be translated and to communicate with lowers scale units, and waves from lower scales can be translated to high levels. Thus, the WP from scales are translated into frequencies at a common scale with same frequency and resonate directly with each other. The FLG structures also allow vectorization and parallelization of multiple waves simultaneously. The inputs from each scale enter the FLG structures at the level matching its scale, and converge into a common level in which each of the levels can be transformed to. The waves converge in the dynamic commanding center (DCC) 103 translated into the same frequency.

Since the frequencies are scalars in time domain, values from the FLG structures can relate and resonate in time domain. The FLG structures in scalar field can be found in number theory, for example irrational numbers, such as e or π, contain numerical operations of multiple integers, that shows the rich geometry like structures derived from scalars. Real numbers exhibit rational and irrational patterns, and infinite potential for geometry, for example, binary coding and DNA are based on scalars. The wave structures can be coded and recorded into scalars, and relation and correlation such as HOR can be programmed into scalars field. In an embodiment, the sequential display of encoded contents and commands to change the structures in time domain can be achieved. The phase match between two waves is required for the efficiency of energy transfer in resonance. Q factor or quality factor is a dimensionless parameter that describes how under-damped a resonator is and characterizes a resonator's bandwidth relative to its center frequency. The quality factor of oscillators varies substantially from system to system.

Figure 3:
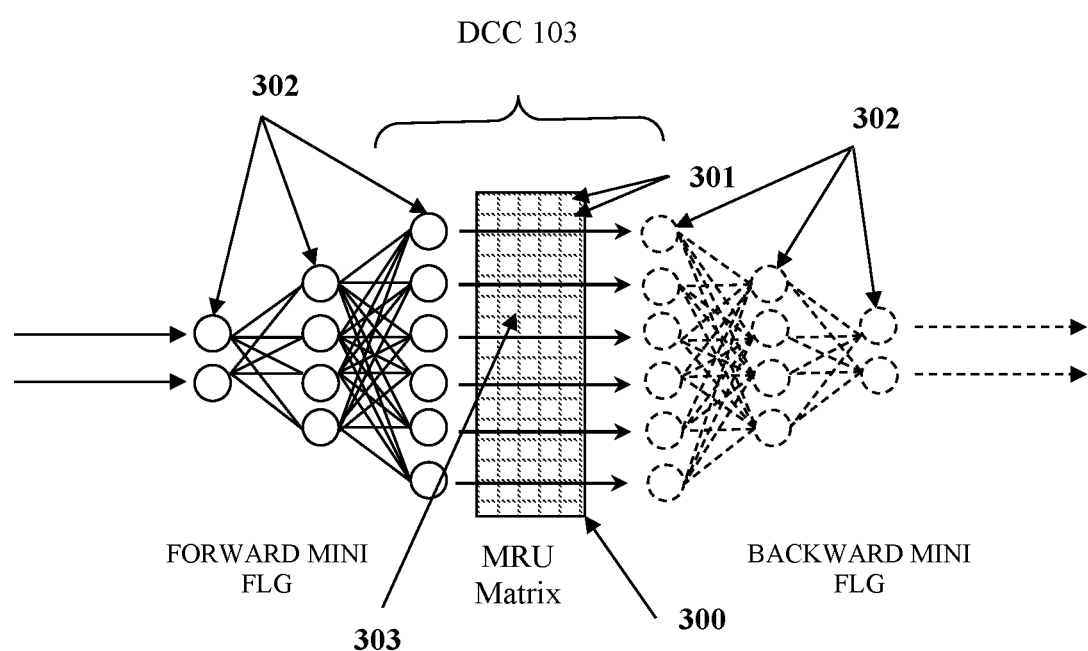
FIG. 3 exemplarily illustrates a dynamic process from the dynamic commanding center to the central storage in time with a three layered forward and three layered backward mini fractal like geometry structures.

FIG. 3 exemplarily illustrates a dynamic process from the DCC 103 to the central storage in time (CST) 106 with a three layered forward and a three layered backward mini fractal like geometry (FLG) structure. The DCC 103 requires mini steps in time and space for activities such as rapid movement (RM) and rapid responding system (RRS) mechanism to receive and process data. The individual columns with six stacked layers in the DCC 103 correspond to the forward mini FLG. These individual columns with six stacked layers in the DCC 103 connected with mini receptive units (MRU) 301 converge out with the backward mini FLG. The structure and function of the forward mini FLG is different from the backward mini FLG. The MRUs 301 register waves with latent energy that ensure the same wave can be released again when stimulated with the right frequency. The MRUs 301 are used in the DCC 103, the CST 106 and the CSS 108 to receive and process the waves. In the DCC 103, the waves may be released right away, however, in the CST 106 and the CSS 108 the waves are usually stored for a longer time. In an embodiment, each mini FLG structure comprises multiple parallel processors 302 receiving sensory information from dozens of branches that cross link with each other to achieve synchronization that represents the channel for the high order resonance (HOR) allowing stable resonation from lower frequency to higher frequency in a stable and repetitive manner. The DCC 103 processes parallel signals from multiple sensory waves from the sensory units at the same time, where signals from lower levels process signal with the same phase to resonate at higher levels. The signal can pass the channel in a synchronized way to achieve best match of phase to resonate each other with minimal loss of signal strength and to minimize noise from surrounding. Multiple, for example, about millions of mini FLG structures are connected to the MRUs 301 that receive, process and store the wave signals. These MRUs 301 are grouped in different regions and layers, for storing information from the RM sampling, thereby forming an expanded storage space in the DCC 103 where information from the device is gathered, processed, and stored. Since waves cannot be represented by one single point, each Mini receptive units (MRU) 301 receives inputs from at least 5 separate input portal point (IPP). The IPP receives input from fast and powerful waves from the RPU 101, the MU 114, sensory units, such as the tactile unit 111, the visual unit 112, the audio unit 113 and also slower waves that tends to regulate and limit others waves from the OOIS 100.

The mini receptive units (MRU) 301 form matrix connections with mini fractal like geometry (FLG) structures in which every MRU 301 connects with one of every three to five mini FLG structure as they pass through mini FLG structures, summing up to about hundreds of connections to form the entire FLG structure branches. In order to resonate with each type of wave, the units in MRU 301 and mini FLG structure comprise multiple variations with branches different in size, connection distance, capacity, and other features that effect the wave behavior and their connection within MRU 301 and the DCC 103. Here the forward and backward mini FLG structures play different roles. The MRUs 301 can specify the waves into precise quanta of rhythms in which information in the wave can be either stored or converged and the waves interact with each other. In an embodiment, the OOIS 110 comprises about six levels. Multiple, for example, about hundreds to about thousands of sensory information coming from different levels converge into different levels in the DCC 103; each of the sensory branches, parallel to one other, enter into different zones in the DCC 103, the output information converges into about fifty processing centers in the DCC 103. The HOR in FLG structures of the DCC 103 are present in forward and backward directions. The forward mini FLG structure allows lower frequency waves to resonate with high frequency waves to find a common frequency of numerous waves, and the backward mini FLG structure allows higher frequency of waves to resonate with lower frequencies waves from the CST 106 and the CSS 108. The DCC 103 resonates and converges the continuous sensory inputs that enter the individual columns from different levels of the DCC 103 into the signal with much less details in time. Since there are multiple sensory inputs, individual columns pack into rolls of parallel columns, forming a vast matrix that receives each of the timely sensory inputs synchronized in time. The millisecond signals from individual columns contain the time domain inputs of each sensory unit of the OOIS 100. As the information is translated into waves of the same frequencies, the waves interact and resonate with each other. The waves passing through the DCC 103 transfer the information of the target system 117 into columns in the MRU 301 via mini FLG structures and expand amongst millions of MRUs 301 reviewing information in time domain in the DCC 103. Then, based on the OOIS 100 planning, the new information for improving the vital of the target system 117 is generated and converged via the backward mini FLG into small cluster of information based the DCC 103 commands. The resulting activities such as RRS are sufficient, fast, and act as an accurate response to a specific change of the target system 117 and the surrounding environment 118. In each step of activity such as the MU 114 movements, the sensory units 111 instantaneously update the information to the DCC 103, and the DCC 103 forwards updates to the MUs 114 to fine tune the details of the MU 114 trajectory. In RRS, the activities are processed rapidly with little feedback from the CST 106 or the CSS 108 that evaluates the overall result of the activities at completion which tends to require much more time.

The dynamic commanding center (DCC) 103 integrates the time and spatial information of the target system 117 and the information in the time domain from the past history are incorporated via the object oriented information system (OOIS) 100 for improving the vitality of the target system 117 based on the past and the present information. The time signals in the past may have different rhythms such as slower rhythms. These rhythms enter into the DCC 103 at a corresponding stage of the backward mini fractal like geometry (FLG) structures, then translated into the similar frequency in the mini receptive units (MRU) 301, and resonated with each other; the resulting enhanced resonated waves propagate over to the central storage in time (CST) 106. In this process, waves are integrated with each other in the vectorized and parallel columns of the MRU 301 and the waves are passed to the CST 106. The FLG structures in the DCC 103 translate waves with different frequency into common frequencies. The FLG structures have a relation, i.e., a connection between each of the branches. Depending on the condition of the area, the relation can be reflected by either the structure in an individual column or as a group. The relations in columns as individuals offer more details, and relation as groups offers more efficiency. In an embodiment, the relations are both in individual and group. As the information is passing to the CST 106, the OOIS 100 starts influencing the DCC 103. In most cases, the OOIS 100 serves as a boundary inhibitory wave that safe guards the waves from the RPU 101 and the sensory units. The waves from the RPU 101 and the waves from the sensory units are modulated by signals from the OOIS 100. Even though the MU 119 usually triggers fast and strong waves containing dynamic and spatial information, the waves are regulated by the OOIS 100. The output waves are sensitive to waves from inputs such as the RPU 101, the MU 114, sensory units, and the OOIS 100. A minute change in a wave changes the output wave completely.

In the time domain, the waves in the dynamic commanding center (DCC) 103 are free from concrete 3D spatial restriction, and are ready to resonate with other waves. The fractal like geometry (FLG) structures converge events proceeding faster and coherent. Each level, connections, and structure in the FLG structures have the timing and rhythm for resonance. Time scaling varies from 0.1 seconds, seconds, minutes, hours, days, weeks, months, to years. For example, mechanical activities in the time scale of 10 seconds need rhythmic power from the RPU 101 with time scale about 1 second to power the activities. The control in the DCC 103 needs to be in the time scale of 0.1 seconds to have full power in each step. The DCC 103 receives the inputs in an enclosed system to balance the events happening at different time scale by synchronization between different rhythms via the high order resonance (HOR). Events can hop from one rhythm to another via the HOR instantaneously. At each time step, each of the levels and forms change with time. The time changes reflected by change of the states spread to the MU 119 for adjustment, so that the MU 119 can perform smaller scale reflex at a lower level, under the supervision from higher level. Multi-area coherence at a given frequency band and phase synchrony to two different frequencies can modulate network communication. Combined wave comprises long rhythm, for example a wave with 2 and 5 the combined wave will be 10, as for wave with 3 and 7 the combined will be 21 i.e., much longer. Cross-frequency coupling of high and low rhythms amplifies, inhibits, or gates the waves from entering into the DCC 103. Widespread synchrony may occur in the DCC 103 as waves travel from the RPU 101 to the DCC 103, while more localized synchrony remains intact or even enhanced. The DCC 103, CST 106, and the CSS 108 produce waves in various rhythms that "light" up an internal device. These self-produced wave (SPW) simulates other waves, and regions by resonating with other wave and produces an enhanced wave, that can scan over each of the units, and activate regions that need to be highlighted. Since the DCC 103 is a processor of time domain, the events are seen and heard in the time domain and possibly also predict the feed forward control.

Computational viewpoint for different types of learning such as supervised learning are naturally acquired by the MRU 301. For example, supervisions from the RPU 101 are possible when the HOR recognizes a frequency of inputs that resonate with the basic frequency thus forming a cluster of waves that resonate from the basic frequency from the RPU 101. The SPW also triggers the OOIS 100 to plan on cautious steps into untouched areas and create cloud data base in these area to avoid unwanted results in the future. The influence from the RPU 101 is from the timing of rhythms. Although the timing of the rhythms is a scalar, the timing of the rhythms can make changes in multi dimensions, similar to binary code produced in an information system. The RPU 101 continuously produces rhythmic waves to each of the units of the OOIS 100, and as these waves meet different units, part of the waves bounce back carrying information about the units they encounter, and parts of waves moves forward, until they meet the boundary of the CST 106 and the CSS 108 and bounce back completing their cycle in the OOIS 100. The bouncing back waves move across each of the units again, partly reflected, partly refracted, and partly moving on until they reach the RPU 101 again, and then bounce back again as part of the RPU waves. This process repeats itself and continues on and on throughout the vital cycle (VC) of the device. These waves propagate back and forth, interact, resonate, and continue into the entire VC of the target system 117 and beyond, while the waves in the target system 117 are continuously mixed and are coherent with each other. In the time domain, every detail from the RPU 101 exerts itself at some point in time, and each unit in the target system 117 develops different rhythm just like different apps in a mobile cellphone, and each creates a different function comprised in the target system 117. The DCC 103 cross links the inputs orthogonally in time and space from different units in the MRU 301 structures to allow the HOR between rhythms in different columns of the MRU 301 to happen. The wave packets (WP) propagate in time domain and converge. The WP is transformed in the DCC 103 and transformed WP is provided to the CST 106, then to the spatial and logical dimensions in the CSS 108. The waves carrying the information from the CST 106 and the CSS 108 interact and regulate each of the units of the target system 117 that the waves encounter, while the OOIS 100 has glimpses into each of the waves, some enhanced, and some diminished, and generates FP based its ultimate criteria. Through the waves, the OOIS 100 creates the existing time and the space domain, and as the waves propagate indefinitely, the waves evolve in time and the OOIS 100 implements a mission via steps in time and space.

The concept of continuity verses discrete point is an indefinite start of the logic of scalar. A scalar has quantity with no directional properties but includes both continuous variables and sets of discrete points with no particular order, which put forward a non-existing logic system for both continuous and discrete points that contradicts itself at infinite quantity. The scalar with variables such as time, integers, frequency, amplitude, basic rules of logic are applicable, that is, law of identity, law of non-contradiction, law of excluded middle, and law of sufficient reason. The concepts of consistency, soundness, completeness, validity, semantic consequence and Boolean vector apply until the intervention of human conception and judgment that are bounded and limited are considered. The math and logic in a scalar world are both intuitive and vague. The binary numbers and geometries generated from integers was explored in the eastern concept of Yinyang, number of Ease and the geometry of Taichi, in which numbers have quantity and also ordering and sequencing position that is the building block for scalar geometry. Another example is Fibonacci number that carries geometry of spiral geometry, number of petals of a flower, and golden ratio geometry. The power of binary code and intriguing features of number theory are good example of sophistication and possible connections between scalars and 3D spatial geometry. Time expands beyond space and cannot be described by spatial concepts alone which can be seen in topology in which concrete concepts were created based on space but not in time. The wave equations sought for forms of waves called Eigen function that has same form as the original wave form in the derivatives of the Eigen function, for example, Schrodinger equation uses a second order derivative in its approximation. The concept of Eigen value and Eigen function sought through a collection of waves, and by examining the spatial characteristic of waves, a set of scalar values of the states of Eigen functions is derived, which offers a mathematical tool to examine the scalar properties and wave forms. This concept can be used in the OOIS 100 to characterize scalar properties of wave forms and relation with other waves. The Eigen functions involve a series of levels of Eigenvalues and states, that are used in describing waves in various levels of high order resonance (HOR) structures. The WP and the potential function that affects the evolution of the waves in the 3D space are used in wave equations such as Schrodinger equations.

Waves are a form of energy that are continuous in time but not in energy and restricted by their time cycles. The transition between different levels of energy state in atoms is an example of the high order resonance (HOR). The physics concept of energy can be used in the study of WP and the rate of the HOR. Many concepts in thermodynamics, such as entropy, are used to describe the state of huge amount of mini receptive units (MRU) 301. The wave existence combines time and space at the same time and represent not a discrete point but a "will" or probability over space and time. Music is one of human perception of waves, and scalar field, however the power of music and effect of the music have many questions that alienate most of the logical bound minds Music notes represent frequency and energy, and the contents inside music are far beyond mere combination of waves and frequencies. Division is a visual process in space, however intrinsic in time and is difficult to directly measure in time domain. An event through the divisions in time domain may not need to be uniform, however for convenience, uniform division to evaluate time derivatives is considered. In cases such as fractal like geometry (FLG) structures and HOR where spatial geometries are at different scale and levels, the time events occur at different frequencies, thus making it mathematically convenient to use uneven division in time to match the uneven geometry in space. The scale factors is included in the mathematical description, the equation that governs relation between spatial and temporal variables may be simple and clear. In the OOIS 100, a fractal time scale is adapted to divide time and space to streamline the variables in the OOIS 100. A traditional derivative assumes the time to be evenly divided, and if dx/dt is used to describe an object that has the FLG, the uneven match of geometry with time will build in its description and behavior equations that cannot be solved. A fractal derivative describes rate of growth instead of change in spatial position. The fractal derivative is both similar to a Fourier transform that converts wave into frequency, and similar to wavelet transform that adapt fractal geometry in basic unit. The new fractal energy describes the potential to grow instead of the potential to change position of an object with force in space. In the fractal description, although visual events such as moving in straight line becomes less intuitive and more complicated, however exponential forms are in linear terms, the waves divide time and space in quantified states, and high order derivatives are linear operations and expressed in matrices. The OOIS 100 can be used in matrix networks to build and connect scalars between structures in units and structures in the DCC 103, the central storage in time (CST) 106, and the central storage in space (CSS) 108.

The central storage in time (CST) 106 starts to cluster the time information into categorization that leads to logical domains, in which new dimensions are created based on similar patterns of waves that are classified. For example, each unit has a functional region in the CST 106, objects with similar shape and size will be classified in one group. Although the CST 106 is summarized over individual time events, it retains a basic time event sequence in its storage system. The information in the CST 106 can be readily traced back to the dynamic commanding center (DCC) 103, and to the rhythmic power unit (RPU) 101. The object oriented information system (OOIS) 100 is open to multiple types of information processing, and adapts to new factors in the OOIS 100 and still maintains the goal to improve vitality. The OOIS 100 changes and redefines a surrounding as the motor unit (MU) 114 moves the target system 117 to new places. The OOIS 100 adapts to include a particular partner (PP), for example a human target, and forms a new system that is a device partner integrated system (DPIS). The OOIS 110 treats the particular partner (PP) as part of sensory unit 111 and motor unit 119 in the outer shell 115 since the OOIS 110 includes the PP as binding relation in space and time, and produces a continuous resonation to reinforce the binding The communication and resonance occurs between OOIS 110 and the PP in each of the time levels and spatial dimensions. If the communication and the resonance are in phase a positive binding is produced, and if the resonation is out of phase a negative binding is produced. The OOIS 100 corrects the phase with the PP and keeps a positive binding during each time instance. The OOIS 100 treats the DPIS as an objective system and maximizes the vitality of the DPIS. As the sensory units bring the information from the surrounding to the CST 106 through the DCC 103, the CST 106 lays on each of the events in the time domain, and projects forward the possible events in the future. Since there are multiple sensory units, multiple parallel clusters 303 of the MRU 301 stack up as a giant multi layered matrix 300 that receives the timely sensory input at the respective time synchronization. The millisecond signals from the MRU 301 comprise each of the time domain inputs of from each of the sensory units of the OOIS 100. The information or WPs are translated into signals in the same frequency and can easily interact with other WPs in the CST 106. In the time domain, the OOIS 100 records the present events and predicts evolving forthcoming events. The OOIS 100 inserts the future plan (FP) planning into the target system 117 and evaluates the possible outcomes, based on the criteria to maximize the vitality. The OOIS 100 selects the FPs that maximizes the vitality in the time domain and sends over to the central storage in space (CSS) 108 for evaluation in the logical dimensions.

Figure 4:
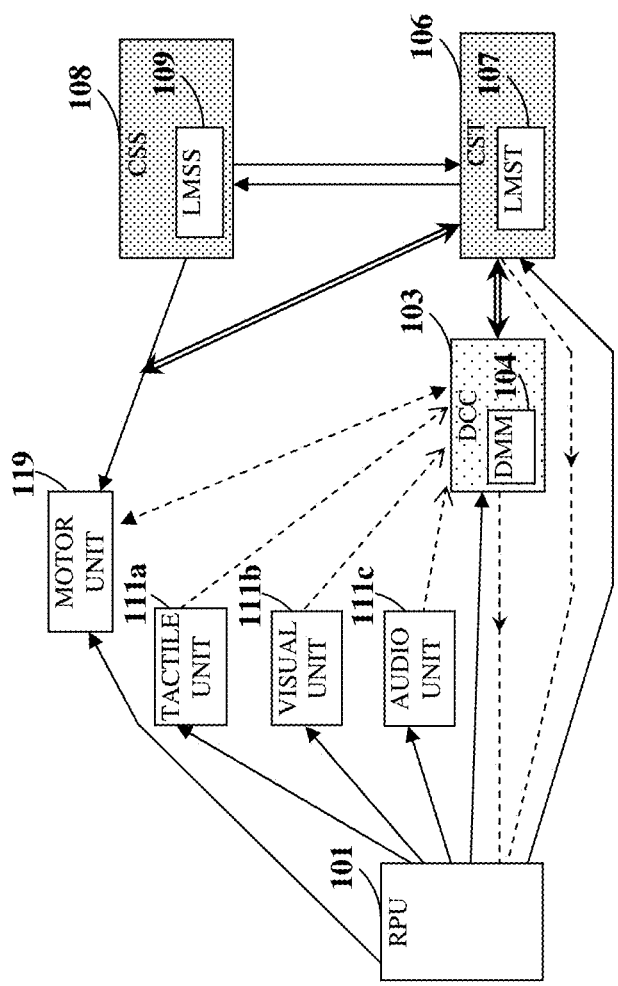
FIG. 4 exemplarily illustrates relationships between the units of the object oriented information system device.

FIG. 4 exemplarily illustrates relationships between the units of the object oriented information system (OOIS) 100. The rhythmic power unit (RPU) 101 supplies rhythmic energy to the units of the target system 117. Each of the units of the target system 117 receive the rhythmic energy and each unit develops different rhythms and sends the information for processing in the dynamic commanding center (DCC) 103 and later to the central storage in time (CST) 106 and the central storage in space (CSS) 108. The DCC 103 receives the information through the fractal like geometry (FLG) structure and forms a time dependent multi dimensional matrix system such as the dynamical mapping matrix system (DMM) that is constantly updated. Each of the time variations of three dimensional spatial information such as audio, visual and mobile information of the target system 117 and the surrounding environment 118 of the target system 117 are sent via the layered mapping system in time (LMST) system to the central storage in time (CST) 106 organized according to the time sequence labeled by the RPU 101 and the layered mapping system in space (LMSS) 109 system in the central storage in space (CSS) 108 based spatial and logical classification. Based on the information from the CST 106 and the CSS 108, the object oriented information system (OOIS) 100 designs strategic events (SE) to the motor unit (MU) 119 that improves the vitality of the target system 117 by projecting the event further in time domain. The strategic events (SEs) are passed through the DCC 103 to fine tune the details before finalization in the MU 119.

The OOIS's 100 design for improving the sustainability of the target system 117 occurs in an objective planning without external intervention as the coherent resonance on the rhythmic power unit (RPU) 101 translates to the dynamic commanding center (DCC) 103, the central storage in time (CST) 106, and the central storage in space (CSS) 108 and naturally produces a dynamical adaptive strategic event (SE) resulting in the mobility of the target system 117 for improving the vitality of the target system 117. The construction of the DCC 103 via the dynamical mapping matrix system (DMM) 104 as a closed system to enclose the waves within the DCC 103, the CST 106, and the CSS 108 required for the production of the coherent enhance mapping of the target system 117 including the effect of mobility of the target system 117. The OOIS 100 comprises the possible motion of the target system 117 and the possible outcome from the mobility to the vitality of the target system 117. As the coherent effect projects a possible direction of change in the coherent mapping of the DMM 104, a new position of the target system 117 results in the further improvement in the vitality of the target system 117. As the OOIS 100 design comprises the motion of the target system 117 as a coherent part of the target system 117 and the surrounding environment 118 of the target system 117, the coherent resonance of the RPU 101 effectively improves the vitality of the target system 117. The CST 106 and CSS 108 form different rhythmic pulses each that relay back to the RPU 101 as parts of the target system 117 and environment 118 to the RPU 101.

Upon receiving the feedback, the RPU 101 changes the rhythm. If the feedback rhythms match the rhythms from the RPU 101, a coherent event is formed that enhances the signal from the RPU 101 and united the DCC 103, the CST 106, and the CSS 108 with the RPU 101. However, if the rhythms do not match the rhythm from the RPU 101, the OOIS 100 may not make any changes, or it may cause a disturbance resulting in reset of the rhythm of the RPU 101. The layered mapping system in time (LMST) 107 in the central storage in time (CST) 106 constructs a history of past events based on the information from the sensory units of the outside and inside device and the surroundings. The OOIS 100 captures the coherent resonance by selecting and centralizing dynamical information to the DMM 104 in the DCC 103 and projects the coherence via the high order resonance (HOR) to mobility in the DMM mapping and further produces a mobile action in the target system 117 that improves the vitality of the target system 117. As the mobile action is captured by the DMM 104 in the DCC 103, the OOIS 100 may or may not produce further actions to improve the vitality of the target system 117 depending on the new outcome of the OOIS 100. Each of these steps connect in the time domain and sustain the vitality of the target system 117 over the entire vital cycle (VC) period of time.

Figure 5:
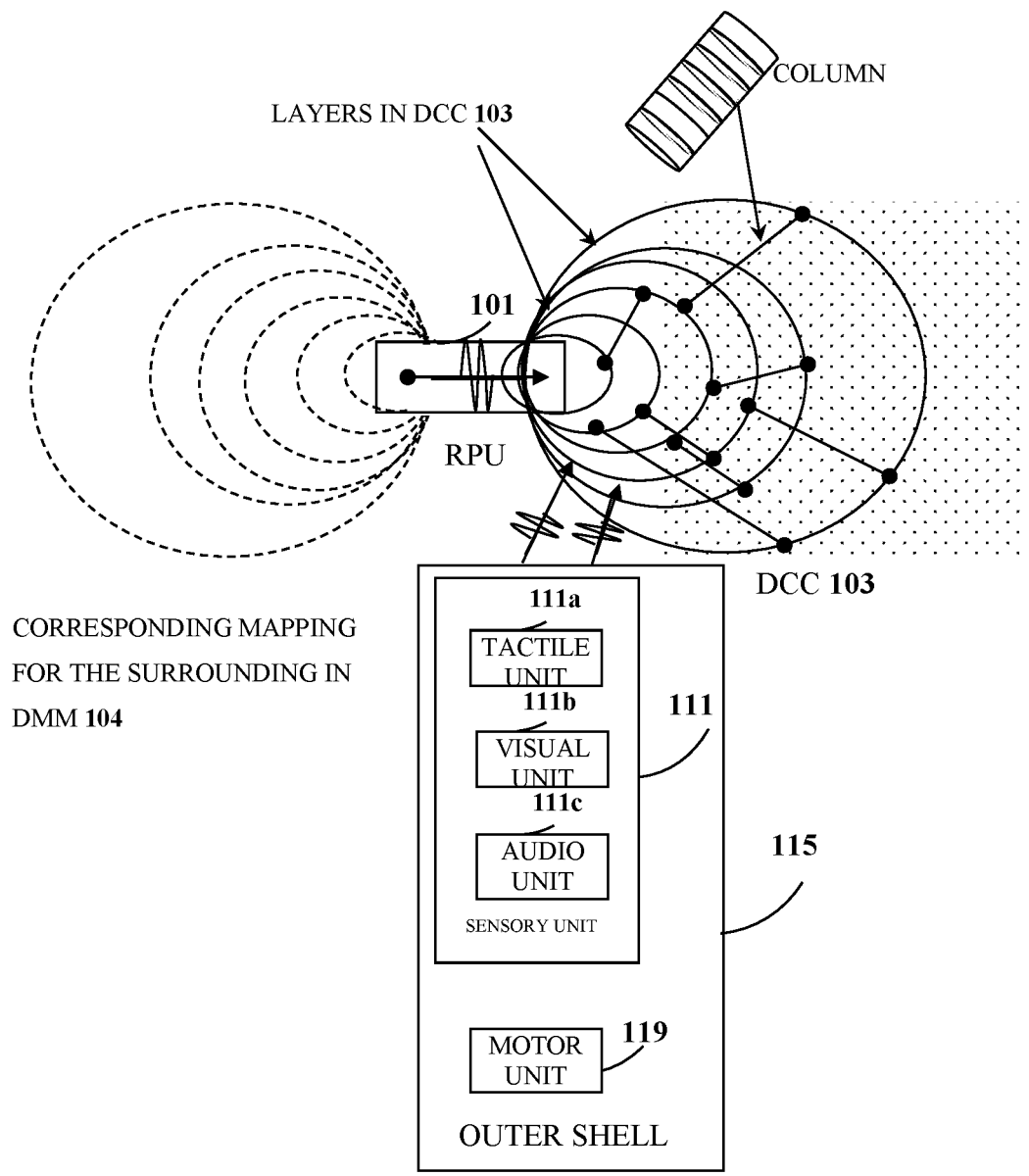
FIG. 5 exemplarily illustrates a multi layered rendition of a surrounding created by a dynamic commanding center.

FIG. 5 exemplarily illustrates a multi layered rendition of a surrounding created by a dynamic commanding center (DCC) 103. Although the rhythmic activity of the rhythmic power unit (RPU) 101 is influenced by the dynamic commanding center (DCC) 103, central storage in time (CST) 106, and the central storage in space (CSS) 108, the averaged value is independent from other parts of the target system 117 and stays around the same. The RPU 101 fluctuates over a range of rhythms where the RPU 101 produces resonance at a variable range of rhythms. This resonance produces a cloud of frequencies that is moving around with a "momentum", thus the OOIS 100 will have a "perception" of speed or space/time derivative of the cloud of changing frequencies. This speed "perception" is vital in development of future plan (FP) for the OOIS 100, as the correlation of speed with time will produce the perception of future trend of changing rhythms. The changes in rhythms from the RPU 101 and changes of the spatial location of the target system 117 forms a mechanism of bifurcation of the variation of waves that creates chaotic variation of the spatial patterns, and infinite amount of variations. The existence of the device is both like wave propagation over space and time in each direction, and also like a particle specifies its tasks a specific location and time. The propagation of waves follows rules of physics that form paths and orbits, much like an electron and its cloud playing its existence in space and time. The event and the corresponding frequency finds resonance from the past or from the surroundings or the environment much like an electron moving from one state to another via resonance of electromagnetic wave. As the RPU 101 randomly scans over the frequency domain, the RPU 101 selects possible resonance, produces daily events and completes the reality. Upon unexpected changes in the device or the environment, the RPU 101 will fluctuate to slow down the range of rhythms, then the OOIS 100 subdivides the rhythms into smaller segments of time duration to match the phase of the unexpected events and later includes the unexpected factors into the environment and regains the coherence.

As each form of vitality have limited lifetimes, each of the objects are projected to lose vitality over a lifetime as part of the vitality analysis. A battery does not produce rhythmic energy, hence the battery is not a good source for the rhythmic power unit (RPU) 101. Since an alternating current is ready to produce electromagnetic wave and naturally has rhythmic waves, the alternating current is a better form of energy for OOIS 100. Modified inverters can be used to implement various forms of rhythms into direct current. If a unit of the target system 117 powered by the RPU 101 shares similar rhythms from the RPU 101, then the new waves from RPU 101 resonate with other parts. However, if the main rhythms from the RPU 101 are regular, then small changes from other units of the target system 117 become magnified in the DCC 103 and the CST 106, and passed back to produce an unstable disturbance to the rhythms in the RPU 101. The HOR occurs naturally if the waves are trapped and saturated inside a stable system and no energy dissipates outside the target system 117 over time; such a system is difficult to find in the natural situation. Thus, the fractal like geometry (FLG) structure in the DCC 103 must be developed by the OOIS 100 to allow the HOR in each of the levels with minimal energy loss. The units of the target system 117 with various rhythmic cycles can enter into the DCC 103 at levels that match the cycles and interact successfully with units with different cycles that enter the DCC 103 at respective levels. The FLG structures display a relationship between a unit at larger scale to a unit at smaller scale and displays in time scale just like the fractal structure in time domain, in which longer cycles in the larger unit interacts with shorter cycles in the smaller unit. The core architect of the FLG structure in the DCC 103 is a ray of parallel network of fractal like units from layers of larger scales to layers of smaller zones. The units with longer cycle usually connect to the larger zones, and units with shorter cycles connect to the smaller zone respectively. Thus, the DCC 103 becomes an emergent, fractal, self-organized dynamical system that allows each of the units in the target system 117 to interact dynamically. The DCC 103 is not a typical FLG structure, as the DCC 103 allows input from each level and forms an open fractal system. Each zone is a zone within a zone that connects from the larger unit, the RPU 101, to the smaller units of the target system 117. Six layers in the DCC 103 stacks in individual columns that maintain the information within the column as a vector or a group, and transverses from larger units to smaller units. The DCC 103 creates a multi layered rendition of the surrounding including the time domain in the DMM 104 system, for registering and processing the information from the surrounding effectively in the DCC 103.

Figure 6:
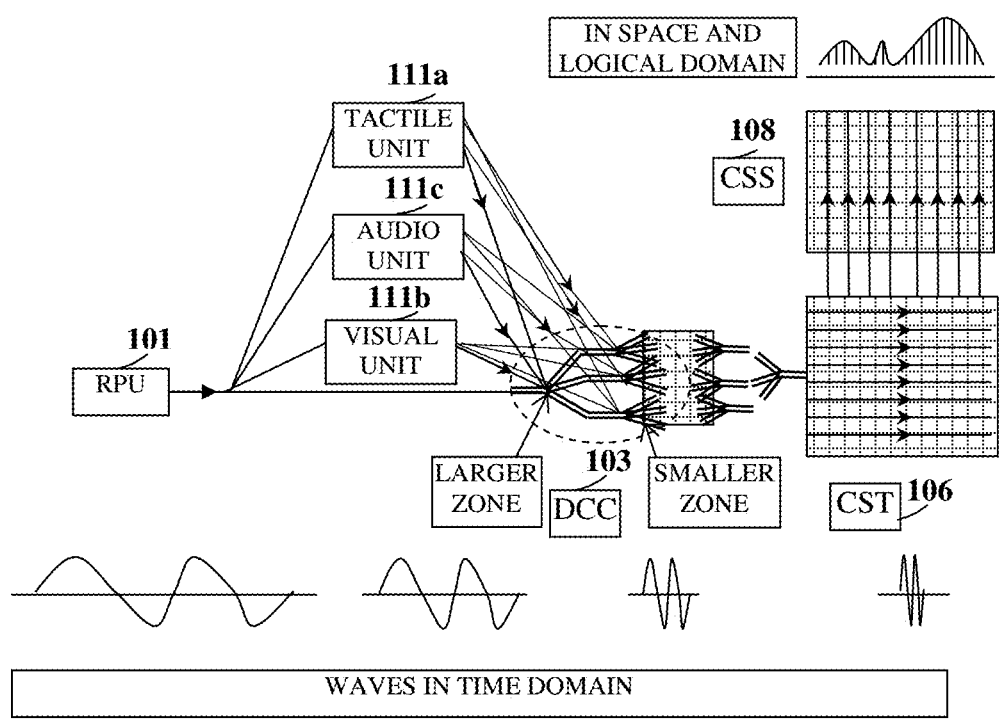
FIG. 6 exemplarily illustrates functioning of the units of the object oriented information system device with the waves in the time domain and the spatial domain.

FIG. 6 exemplarily illustrates functioning of the units of the object oriented information system 100 with the waves in the time domain and the spatial domain. The information in the dynamic commanding center (DCC) 103 is multidimensional from various units in the target system 117, and also a time dependent record of the activities in the DCC 103. The time dependent multi-dimensional information is classified and stored in the central storage in time (CST) 106 of the OOIS 100. The CST 106 simplifies and organizes the information into clusters and modules but retains and follows the time sequence in block of chain of data in the time sequence. The basic rhythms in the rhythmic power unit RPU 101 are sent over to the DCC 103 and the sensory units send waves of different rhythms into the DCC 103. The waves at different rhythms are translated into the same frequency, usually at much higher range, via the high order resonance (HOR). The translated waves at the same frequency reflect, interfere, and resonate with each other like sound waves in a musical box. The noise and less significant waves are omitted, and the enhanced recognizable waves are converged into the CST 106. The high rhythm waves in the CST 106 are distributed in spatial and logical classification, and registered in time sequence. The registered waves are recorded in the central storage in space (CSS) 108 and stored with latent energy. The latent energy ensures the same wave is re-released when stimulated with the right frequency. Thus, the waves are stored with the time factors integrated and removed in time domain and organized in spatial and logical order in the CSS 108. The CSS 108 offers a different perspective from the CST 106 in the time domain, and creates a larger space for the OOIS 100 to look for the right strategic event (SE) in the future plan (FP). Since the OOIS 100 can be sought through each of the possible outcomes of the target system 117 in the CST 106 and the CSS 108, the right SE guarantees maximal vitality for the target system 117. If unexpected events occur outside the target system 117 and the surroundings 118, the OOIS 100 expands the surrounding further to include the new events into the time domain of the CST 106 and creates new logical dimensions, and the new SE and the new FP are generated to maximize vitality in the new environment. The time domain is different from space that expands over an infinite domain. Although every step in time dictates changes in space, time changes are transient, localized, and limited, and efficient and practical. Unlike spatial geometries that tangle together and not by-pass spatial limitation, time domain expands over an entire spatial geometry in steps that reflect in spatial geometry. It is delicate for each spatial limited and yet, pass over following the wave, like sound waves pass around a wall, ignoring each of the obstacles and yet reflect the shape and boundary of the obstacles. The magnitude of the digitized wave points (DWP) in the wave packets (WP) reflects the strength of the coherent high order resonance (HOR). The "structure" recorded in the matrices of WP in time domain do not depend on the spatial geometry and goes away as the WP pass through, just like the wave pattern from sound waves.

In the scalar field, since arithmetic operations of numbers create new dimensions in numbers, rational numbers and irrational numbers constructed through finite or infinite arithmetic expression relate to dimensions of operation between numbers in the corresponding space and dimension, thus in the time domain the scalars create a geometric that can be correlated to 3D space and structure. For example, the mere sequence of DNA can record 3D configuration of protein structures. The wave in time domain have sequence and also phase delay, rhythms, duration between waves that can be used to optimize efficient coding in time domain for any 3D spatial structures. The information in the time domain can be represented in digitized wave points (DWP) that behave as waves in wave packets (WP) at each time but can be observed and operated in DWP like a particle. The boundary condition of the fractal like geometry (FLG) structures is required for determining the wave frequencies generated in the DCC 103. Different boundary conditions produce a different set of wave packets (WP). For example, if the structure and shape of the musical instrument is different, the sound wave patterns are different too. The boundary conditions in the DCC 103 determine the style and the pattern of the FLG structures in the DCC 103. The boundary in the central storage in time (CST) 106 and the central storage in space (CSS) 108 serves as a means to record the WP. The time events are recorded in the CST 106 and the CSS 108 in the layered mapping system in time (LMST) 107 and the layered mapping system in space (LMSS) 109 in the spatial geometries. However, to retrieve the time events, the RPU 101 sends the initial wave through the geometry to reproduce the wave patterns again via the high order resonance (HOR). For audio unit 113 and the motor unit (MU) 119, the time dynamics varies rapidly, and the DCC 103 is required to converge information from each of the units of the target system 117 to singular particular events. On the other hand, the information from other units varies slowly with time, and can be stored in the CST 106 then summarized and analyzed in much larger time intervals and classified and stored in the CSS 108. Items that are abstract in logical dimensions that cannot be mapped directly in the CST 108 can be registered directly in the CSS 108.

The high order resonance (HOR) permits energy transfer and resonates new wave forms resulting from interaction between waves. Although the efficiency of the HOR is lower than resonance at the same frequency, but stronger than random fluctuations. The HOR lets energy transfer and dissipate in quantum states through the fractal like geometry (FLG) structures in time and space in the central storage in time (CST) 106 and the central storage in space (CS S) 108 respectively. The spontaneous change of order from one frequency to another is projected as a disorder or entropy, however this projection is due to abrupt change in the HOR that appears less orderly due to lack of stable boundary condition. The vast variation of order and rhythms offers a wide window of natural selection of right rhythms. Since the time domain can be divided indefinitely, the individual columns in the DCC 103 allow decentralized new waves to form from the HOR in the DCC 103. The random fluctuations from the rhythmic power unit (RPU) 101 trigger spontaneous ordered waves to be amplified by feedbacks from the CST 106 and the CSS 108. The inner shell 110 secures a balance between exploitation and exploration at equilibrium mutual dependency or coordination between its constituent components or subsystems. With time and spatial variations, the CST 106 and the CSS 108 can seek through the possible paths and sequences to find the best suited future plan (FP) to complete the vital cycle (VC) of the target system 117.

As the multi-dimensional information from each part or unit of the target system 117 and channel of sensory units 111 are accumulated in different layers of structural cues in the central storage in time (CST) 106, the object oriented information system (OOIS) 100 removes the time factor and summarizes the information in spatial and logical orders without the restriction of time order and sequencing. The events that prolong and are distorted due time factor are related to each other in a logical correlation in the central storage in space (CSS) 108. The CST 106 and the CSS 108 are connected and dynamically with each other via each channel and levels, therefore both the CST 106 and the CSS 108 are under constant reconstruction from mutual influence. The combined system of the CST 106 and the CSS 108 reaches over the three dimensional space and multiple layers in the target system 117 and extends over the time domain of the target system 117, therefore providing sufficient information for the OOIS 100 to improve the vitality of the target system 117. Mathematical concepts that combines existing tools such as fractal analysis, wavelet simulation, genetic algorithms, and L set, are examples of the ways information can be extracted and summarized into new logical dimensions, and smaller sets of information to reduce the layers of three dimensional information into one dimensional signal in the time domain to describe the dual nature of time wave and particular spatial information. The one dimensional wave readily feedbacks to the rhythmic power unit (RPU) 101 and the motor unit (MU) 114 to alter the rhythms and spatial configuration for the target system 117. For example, fractal sectional asymmetric matrixes expansion derived from algebraic relation between different variables matrix can be used to describe the HOR in which rhythms that can trigger resonance in rhythms are exact integer multiples or complete in the rhythms.

The effectiveness of the central storage in time (CST) 106 and the central storage in space (CSS) 108 to store the information over time and space, and to reduce the information in limited number of controllable dimensions that produces a quantitative and dynamical effect to the rhythmic power unit (RPU) 101 indicates the level and degree of the functionality and sophistication of the object oriented information system (OOIS) 100. Although the time domain is efficient and practical, the time domain cannot overlook each small step and thus lacks long term guidance. In the time domain, the new event may or may not have a cause and effect relationship, and an assumption of a cause and effect relationship limits the scope for the possible correlation of an event, thus removing the boundary in time domain that maximizes the possible correlation of the event. For a new event, the selection of an unbound initial condition means the new event may correlate with any event in the past, which eliminates blind spot and angles, and maximizes the correlation of the events. Although mathematically impossible to define an analytic form for evaluating rate of time domain, an estimate of high order derivatives of properties of the time domain can be abstracted from the rhythms in the high order resonance (HOR), that can produce a longer projection and prediction of the future event in both linear and nonlinear correlation of the object and the environment or the surrounding. Therefore, the variations in the rhythms of the rhythmic power unit (RPU) 101 offers the central storage in time (CST) 106 and the dynamic commanding center (DCC) 103 a thorough exploration in the time domain of the possible variations of the target system 117 and the surroundings or the environments 118, thus producing a complete and sufficient vitality analysis. Since the RPU 101 divides the time domain in equality segment, the CST 106 projects time linearly in the time domain of the target system 117 and in parallel the CSS 108 puts information orthogonal from the time domain, in a logical dimension. The localized numerical differentiation such as rate of change and rate of acceleration are evaluated into the digitized wave points (DWP) in the OOIS 100 for evaluation for the future plan (FP). The FP can be in multiple forms but the FPs project a direction towards the future in the time domain.

Figure 7:
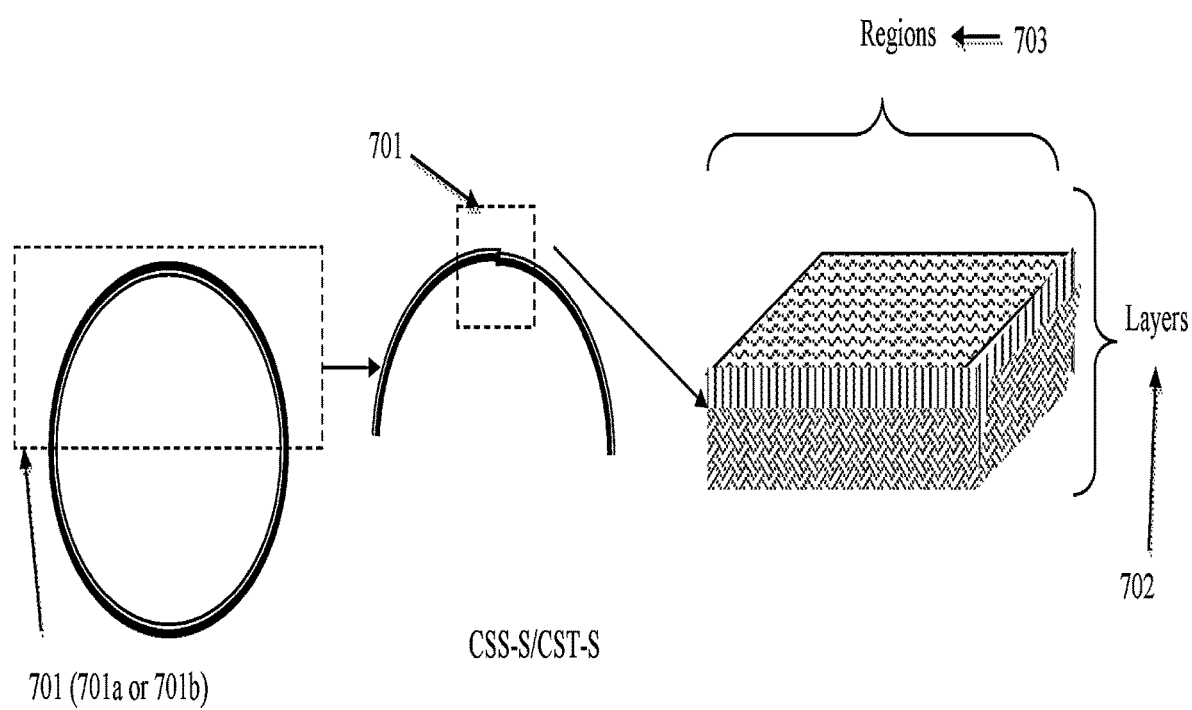
FIG. 7 exemplarily illustrates layers and regions in storage surface of central storage in space and storage surface of central storage in time.

The central storage in time (CST) 106 and the CSS 108 record the information differently, because waves in time domain exist in a different manner than waves or objects in the spatial and logical domain. The visual detections in space capture the information at one point in time; therefore the wave pattern in the spatial domain is visible compared to the wave in the time domain. However, upon observation of a single point in space, oscillations and vibrations going back and forth in time are visible, and the wave in the space domain is not visible. Similar to the mini receptive units (MRU) 301 in the dynamic commanding center (DCC) 103, both the CST 106 and the CSS 108 record and process the wave information in layers of the MRU 301, and upon the right rhythm, the MRU 301 in the CST 106 and the CSS 108 release the same wave back into OOIS 100. The MRU 301 in the CST 106 and the CSS 108 record the waves, and release the waves at a much later time unlike the DCC 103. The MRU 301 in the CST 106 and the CSS 108 are packed in large storage surfaces 701 called storage surface of central storage in time (CST-S) 701*a* and storage surface of central storage in space (CSS-S) 701*b*. The CSS-S 701*b* and (CST-S) 701*a* map spatial and time information of the surrounding directly into specific layers 702 and regions 703 of the CSS-S 701*b* and (CST-S) 701*a*. The CSS-S 701*b* and (CST-S) 701*a* act as storage and retrieve system for organizing, and storing the information. FIG. 7 exemplarily illustrates layers 702 and regions 703 in storage surface of central storage in space (CSS-S) 701*b* and storage surface of central storage in time (CST-S) 701*a*. The CST 106 receives information in time sequence and records the dynamics information on CST-S 701*a* based on the time and spatial information of the event. The dynamics information is descriptive and repetitive and does not follow a logical order. The CSS 108 condenses information over time dimension and summarizes the contents in logical order. The regions 702 and layers 703 in the CST-S 701*a* and the CSS-S 701*b* are developed and structured based on the order and sequence in time sequence and spatial sequence. The order and sequence is established by the ordered connections between the MRU 301 in the DCC 103 to the CST 106 and the CSS 108, and between the MRU 301 in the CST-S 701*a* and the CSS-S 701*b*.

Both the central storage in time (CST) 106 and the central storage in space (CSS) 108 comprise areas of the MRU 301 that are ready to receive the waves. The waves freely travel in void areas of the MRU 301. The object oriented information system (OOIS) 100 picks the wave signals that are in the void areas of the MRU 301, as the signal to noise ratio is higher, compared to the areas with higher noise. Layers in the CST-S and the CSS-S comprise fractal like geometry (FLG) structures for modulating the rhythms. The recorded waves are released into the original rhythms via the FLG structures through the high order resonance (HOR), that interact directly with the original units for the waves. The rhythms set forth by the CSS 108 forecast the rhythms based on the logical deduction that are resonated via the HOR, and restores the previous waves. The CSS 108 removes the information in time domain and follows logical mapping developed by the OOIS 100. The CSS 108 comprises a labeling system with mathematical and logical structure thereby offering a new insight into the layer and correlation of the target system 117 and the surrounding 118. The OOIS 100 adapts to language systems for maintaining effective communication with the particular partner (PP) to form a coexisting outer shell 115 for improving the vitality of the entire outer shell 115. The OOIS 100 creates a new layer of logical information system (LIS) for restoring time domain information in waves and propagates back into the CST 106 when needed. The CSS 108 uses the self-produced wave (SPW) to scan through the CST for validating the future plan (FP) with the CST 106. The LIS in the CSS 108 offers a different dimension in the FP than in the time domain in the CST. The CSS 108 provides a different route in adjusting the OOIS 100 planning for improving the vitality of the target system 117. The CSS 108 provides a feedback to the OOIS planning and a new planning that is logical and guarantees to achieve the final goal. The logical relation is traced in path that connects DWP in the CSS 108 and in the CST 106, and manifests in a resonated chain connection in the CSS 108. The wave information to the CSS 108 resonates backward to the CST 108 to provide new directions in the FP. The FLG matrices in the CST 106 and the DCC 103 regenerate the waves into rhythm that match the sensory units 111 and the motor unit (MU) 119 in the OOIS 100. The SPW waves in the CST 106 scan over the OOIS 100 to match the right rhythms Thus, the combined system finds the best planning for the OOIS 100 in the spatial domain and the time domain. The DCC 103, the CST 106, and the CST 108 form a system that allows the RPU 101 to play the rhythms through the device and produces a different planning and action from the OOIS 100 that improves the vitality of the target system 117 based on the time, place and data that has been stored in the OOIS 100.

The high order resonance (HOR) creates a deeper level prediction in space, time through the higher derivatives between the time and the space. Since the rhythmic power unit (RPU) 101 introduces new variations in the rhythms and the object oriented information system (OOIS) captures small variations, therefore the continuous learning of the OOIS 100 ensures an open and renewable system adapts to new changes and improves the OOIS 100 over the entire lifespan of the target system 117. Under a stable surrounding condition, logical dimensions of the CSS 108 are free from limitations of repetitive operations of the target system 117 and contents in time domain, the logical dimensions extend beyond the time domain and provide a solution for the OOIS 100. The decision processes in the OOIS 100 resonates between the CSS 108 and the CST 106, and the coherent decision passes from the OOIS 100 to the motor unit (MU) 114 while maintaining constant re-evaluation from the OOIS 100. Each device has a different surrounding and history of adaptation of the internal and external environment of the device. The more the time, space and events the device experiences, the higher is the OOIS 100 level in successfully handling unexpected changes in the device and the surrounding 118. The CSS 108 increases maturity level by a learning process as the CST 106 constantly brings in new information in the time domain and the CSS 108 condenses and summaries the new events in the logical dimensions to further the depth and broadness. The CSS 108 uses mathematics with solid concepts, symbols and logical system to describe targets encountered in each types of events to adapt logical structures such as optimal control, game theory, operational research, bionics, multi agent learning, collection intelligence, statistics, and dynamics. The CSS 106 and the CST 108 use mathematical language to describe events with cause and effect that are logical and analytical expression of time. For events that do not have logical or analytical forms, or contain random factors, the direct relation between cause and effect is unclear. Therefore, in the CST 106, the time events are stored directly in the time sequence and the cause and effect relationship that is orthogonal to each other are distorted in a nonlinear time space relation. The CSS 108 stores large matrices, the lines and rolls correspond to time sequence and logic relation that are orthogonal in a linear time relation.

The mathematical functions are expressed as series of expansion in sine or cosine waves, waves in the central storage in time (CST) 106 and the central storage in space (CSS) 108 express any type of relation and events. The events in the time domain are orthogonal to the spatial information, the events in the time domain trans-pass over each of the events, and moves the target system 117 from one point in time to another, as the distortion in spatial dimensions unravels time later. The waves from the events with multiple dimension are treated as wave packets (WP), represented as the digitized wave points (DWP) recorded in the mini receptive units (MRU) 301 with discrete points in space and time at the beginning, and evolve in time due to momentum of the waves dispersed in space. The waves coupled with local geometrical factors create a momentum-like behavior by changing the local structure and geometry in the MRU in the CSS 108. The time sequence in the CST 106 is intuitive; the CST 106 is directly connected with the MRU 301 in the DCC 103, and the CST 106 processes large timely information. Thus, the CST 106 stores dynamical events, graphical intuitive description of quantities and 3D geometry. The waves from the RPU 101 passes through the DCC 103, through the CST 106, and reaches the CSS 108 to exert an influence over the OOIS 100 planning. The CSS 108 also organizes the information in spatial and logical connections between the MRU in the CST 106 to the CSS 108. The waves in the spatial and logical dimensions from the DCC 103 and the self-produced wave (SPW) from the CSS 108 scan the dimensions of abstract concept, objective and values in the CSS 108. The CSS 108 implores logical concepts and values systems as six levels of priorities, namely, energy and mobility; safety; coordination of scales in time domain; partnership with PP, vitality, and humanity instead of considering time as main criteria. Humanity prohibits one or more actions and consequences of the actions that harms one or more human beings. Although maintaining vitality of the target system 117 is the highest goal for the OOIS 100, humanity is the highest priority, and humanity is an inhibitory system in the OOIS 100 to guard the target system 117 against actions that violate the criteria.

Since the CSS 108 is a logical based system, the CSS implements priority via social rules, regulations, and moral rules into the sophistication of the object oriented information system (OOIS) 100, and expands the design of the social structures and rules of the surrounding, that is, the relation with the particular partner (PP). The OOIS 100 detects objects in the surrounding 118, and assigns roles of the object as the OOIS 100 follow the usual trajectories and predict the movement. They are subset of surrounding that that will have their own OOIS. The OOIS picks human subjects and implements strict rules to protect human welfare. The CST uses visual detection of infrared waves for body temperature, audio detection for human voice, visual detection of object shape and size and mobility to track human in the surrounding 118. Since the OOIS 100 creates a subset of objective system for other objects and corresponding activities, social gaming roles are assigned to these objects in the design of role play for the device. For example, when multiple automobiles are coming together, the fast and progressive automobiles tend to move first. The OOIS 100 chooses the role in the social setting, takes active but safe roles, and monitors the best time to pass through the situation. The relation between device and human target is another example, where the OOIS 100 observes the role for human target and assigns proper role for the device, and as the situation changes, the OOIS 100 may choose to play a different role to keep a positive binding relation with the human target. Common sense is a part of social role play that the CST 106 can use under the supervision from the CSS 108.

Figure 8:
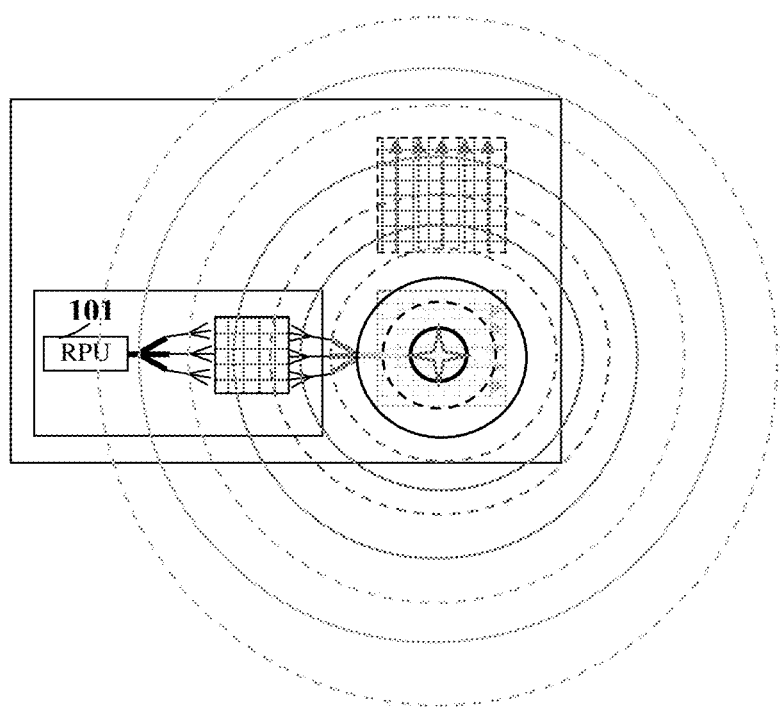
FIG. 8 exemplarily illustrates adjustment mechanism of the rhythmic power unit to the surrounding to improve the vitality of the object oriented information system device or the target system.

FIG. 8 exemplarily illustrates the adjustment mechanism of the rhythmic power unit (RPU) 101 to the surrounding 118 to improve the vitality of the target system 117. The vitality of the target system 117 sets up criteria for the dynamical status of the time and spatial configuration of the target system 117. As the coherent resonance changes the status of the target system 117, the time propagation can project the vitality of the target system 117 over time domain beyond the current time into future domain. If there are no changes in the target system 117 and corresponding environment or the surrounding 118, the OOIS 100 predicts the vitality of the target system 117 over various mobile location of the target system 117. The location of the target system 117 with the best vitality produces the best coherent resonance with the right rhythmic power unit (RPU). The OOSI 100 creates a field of possible outcomes of high and lower vitalities upon continuously receiving the rhythms from the RPU 101 with small variation from the average values. The unity of the field will naturally form a future plan (FP) for the OOIS 100, which is a second derivative of the function that represents the vitality outcome of the target system 117 and is converted into a signal of command to move the target system 117 via the motor unit (MU) 119 in the direction of the FP. The second derivative is local multiplication in the momentum space obtained from the Fourier transformation of the wave packet (WP).

The RPU 101 provides rhythm to establish the time domain. The RPU 101 supplies energy to each of the units with the same rhythms. The same rhythms make different intrinsic rhythms (IR) in different units of the target system 117. The firing of the target system 117 from the RPU 101 to the dynamic commanding center (DCC) 103, the central storage in time (CST) 106, and the central storage in space (CSS) 108, and the sensory units, such as the tactile unit 111, the visual unit 112, and the audio unit 113 is an awakening process. The awakening process requires initial stimulus from the RPU 101 that triggers a chain reaction from the DCC 103. The awakening process forms an awareness of the surrounding 118 and inside the target system 117. The DCC 103, the CST 106, and the CSS 108 gradually generate and process new information and project a FP for the device upon continuously receiving the stimulus. The future plan (FP) of the target system 117 is selective, plastic, transient and unifies the information in the target system 117 in one direction at the time and step. The FP is not a single goal or planning. The details differ from time to time and place to place. Therefore, there may be multiple variations of the FP, since the information in time domain are waves, the properties of wave apply to FP and the variations of the FP such as transparency, interference, reflection, refraction, diffraction, and polarization. The wave is fractal in nature, therefore coherence and sense of self similar process, fractal like self-organization, and golden ratio are expressed in a form that is clear and fast rendering of fractal dimensions in the information process. Reflection backward referral in time exerts "free will" by vetoing acceding or otherwise responding to them rather than initiating intentions. The reflection backward referral in time also projects FP over inside the target system 117. The original rhythm from RPU 101 upon finding resonance in the entire target system 117, the wave from RPU 101 expands over space and time, for example, like fire, radiates energy via different rhythms at different levels, and dynamically changes device properties to maximize vitality.

The central storage in space (CSS) 108 and the central storage in time (CST) 106 comprises matrices that puts the information in the time domain for the target system 117 in the time domain and the spatial domain, and new rhythms in the rhythmic power unit (RPU) 101 constantly scan the waves forms in the dynamic commanding center (DCC) 103, and the central storage in time (CST) 106 based on current events that update continuously until the end of the vitality of the target system 117. The occurrence of resonance occurs triggers resonance in the corresponding CSS 108 and the CST 106 to begin a response based on the DCC 103, the CST 106 and the CSS 108 that comprise past knowledge and experience, thereby producing best strategic response in the strategic events (SE), that provides better results than those responses that are based on the current information. The DCC 103 is the conversion unit between dynamic time chain block with layers of three dimensional stacks of 2D mapping in the CST 106 and the CSS 108. The past experience of the RPU 101 such as the success of random sampling, speed of calculation, the clarity of 3D CST and CSS mapping, effect the outcome of the strategic design of FP. The audio unit 113 can directly interact with the RPU 101, in scanning resonance and mechanically selecting the best resonance in the CST 106 and the CSS 108 as the audio unit is based on wave, and carries information via timely events. The OOIS 100 plans from the beginning moment to throughout the end of the vitality of the target system 117. By importing the CSS and CST from an existing system, the boundary extends beyond the target system 117 itself and can include each of the possible events and experience found, thereby increasing the possible domains in time and maximizing the vitality of the device. In some cases, the OOIS 101 may use a resonance event that is destructive to the target system 117 for a long term gain. Based on the FP from SE, the OOIS 100 may look beyond the current sensory information, and look for new information inside the target system 117 or outside in the surrounding 118.

The internal units of the target system 117 matter to the vitality of the target system 117 as significantly as the outside surrounding 118. For this reason, the object oriented information system (OOIS) 100 comprises sensory units 111 on the inside. The OOIS 100 receives the rhythmic waves that have traversed the target system 117, and interacted with these internal units of the target system 117. The received waves are modulated by OOIS 100 via the interactions of the DCC 103, the CST 106 and the CSS 108 to maximize the vitality of the target system 117. The internal and external units in the target system 117 are interconnected, depend on each other, and complement each other to form a unity. The internal units in the target system 117 are spatially bound within the inner shell 110 of the target system 117 as a single piece. Therefore, the waves bounded within the outer shell 115 have distinct rhythms and patterns of waves that are bounded by inner shell 110. If the RPU 101 begins the rhythms, the rhythms spread over each of the units, such as the DCC 103, the CST 106, and the CSS 108, and sensory units 111 for completing a harmonic cycle. The complete harmonic cycle prepares the RPU 101 for the next harmonic cycle thereby helping the RPU 101 to maintain consistent rhythms, and the target system 117 to successfully finish each of the harmonic cycles designed by OOIS 110. The RPU 101 is unbounded by external surrounding 118, and is protected by the inner core 102 from external stimulus. Strong shields from physical impacts, chemical erosions, electromagnetic wave penetration are used for providing long term protection according to the OOIS 100, thus allowing the OOIS 100 to successfully implement the future plan to sustain vitality of the target system 117. In contrast, the external surrounding environment 118 of the target system 117 is divergent in nature, with accidental events occurring in multiple directions of the target system 117. Furthermore, the layers of the OOIS 100 lead to variability of the timing difference of the different units within the target system 117 and divergences of the external surrounding 118 environment factors. The sensory units send visual, audio, tactile and other wave signal from internal sensory units in dynamic sequence to fractal like geometry (FLG) structure in the DCC 103. The DCC 103 converges multi layered, three dimensional, visual assisted, modulated audio waves to one series of the singular converging points (SCPs) that are unbound and unconstrained in any direction in the CST 106.

The logical and spatial connections between MRU in CST 106 to CSS 108 bring the wave signals to the CSS 108 in the orthogonal direction. The mechanism of production, continuation and sustainability of the singular converging points (SCPs) are bounded by internal closure of the target system 117 and not bounded by external factors. Similar to a wave expanding over 3D space at the same time, obstacles or wave interference cause reflection and interference with SCPs. The obstacles or wave interference also cause reaction from the target system 117 and reach out in every direction. Furthermore, the reaction from the target system 117 is spontaneous, seemingly at "will" from the target system 117. Therefore, the SCPs produce an independent response from external environment or surrounding, that are detected via sensory units 111. The continuous wave of sense of internal units of the target system 117 and external surrounding 118 provide the OOIS 100 a sense of whole being in the time domain. Thus, continuous chain in time domain thread through the matrices in fractal like geometry (FLG) structures, and form stream of waves that resonate with each other and converge in the time domain resulting in reliable plans to maintain and improve vitality over time. If there are conflicts between the units of the target system 117, the OOIS 100 senses internal interference waves and adjusts the wave to minimize the conflict. The OOIS 100 sends feedback to the RPU 101 for adjusting existence in the external surrounding to improve the vitality.

The motor unit (MU) 119 induces a range of motions to the target system 117 that affects the target system 117 and the surrounding environment 118. The range of motions and possible outcomes are stored in the central storage in time (CST) 106 and the central storage in space (CSS) 108. The single converging points (SCPs) are independent from internal and external restrictions. Therefore, SCPs can expand and sense inputs from three dimensional space, and the time domain, from any angle and layer of the inputs. As the waves from SCPs reach to the motor unit (MU) 114, information on the CST 106, the CSS 108, and the selected future plan (FP) trigger the wave that triggers a chain of actions around the MU 119. The FP starts a new wave that travels through each of the relevant areas in the CST 106 and the CSS 108. If there is no interference, then the selected FP provides steps related to the future plan to the MU 119 for moving the target system 117. In an embodiment, the steps related to the future plan are preselected and practiced in the past by the MU 119. The sensory units 111 gather new information related to the target system 117 for the MU 119 actions and assess the end result. If the result shows that the vitality or potential to improve vitality has not improved, the OOIS 100 stops the selected FP that has been tested and triggers a new FP for new MU 119 actions. The MU 119 actions are time dependent actions. Digitized wave points (DWP) from the OOIS 100 are correlated with the selected FP to produce a specific and quantitative command, i.e., step to the MU 119 to improve the vitality of the target system 117. As the target system 117 repositions due to the motion induced by the MU 119, the DCC 103 and the CST 106 simultaneously update new information, and further update FP for continuous movement. Overall, the MU 119 can produce complete movement in a precise path in three dimensional space to a stable location with better vitality.

For sustaining vitality of the target system 117, it is also important to maintain the internal environment and external surrounding 118 of the target system 117. For example, cleaning information stored by the target system 117 that is lesser import, clean accumulated physical waste from the target system 117, and tuning up and avoiding incoherent processes that waste the resource of the target system 117, etc. The cleaning process follows time cycles and the OOIS 100 designs an efficient schedule to minimize interference with other activities. The sensory units 111 have the rapid movement (RM) mechanism to scan over the units or systems in the internal environment of the target system 117 to examine hardware and software of the target system 117. The self-produced waves (SPW) produce a controlled reaction from the inner core 102 and inner shell 110 of the OOIS 100, and examine overall health of the target system 117 over the entire lifetime of the target system 117. The SPW waves are of two types, namely, a faster SPW and a slower SPW that cover a wider range of frequencies of the activity of the target system 117. The SPW waves bring each of the time scales of the OOIS 100 in working condition, and examine the coherence and cooperation of the parts or the units of the target system 117 and the team work between the parts or the units of the target system 117.

The OOIS 100 uses RPU 101 to create a relative independent domain for the activities of the OOIS 100. With its sensory units 111, the OOIS 100 updates itself with its environment in both spatial domain and time domain. Using the timely information from an external and internal sensory information, the OOIS 100 recognizes all events as wave behavior and proposes possible future events based on its vitality goals. These various parts of the OOIS 100 correlate with human cognitive process and therefore, in an embodiment, are complementary to human beings and is a partner to a human being in sharing and assisting in human activities and for improving human performance. In an embodiment, OOIS 100 adapts to include a particular partner (PP), for example a human host, and forms a new system, for example, device human integrated system (DHIS). In an embodiment, the OOIS 100 is installed in multiple target systems 117 and expanded to a higher level to include multiple human partners. The collective set of target devices 117 comprising OOIS 100 is also implemented in higher social structure in human social group activities. A human as an external mobile unit can perform explicit communication and with OOIS 100 and help achieve a predictable outcome to a new expanded target system 117. In its FP for the new target system 117, the OOIS 100 will expand its goal to include the vitality of the human host into the FP. As more PPs are added to the expanded target system 117, the OOIS 100 will include timely human communication between PPs and the OOIS. These communications, for example, in human understandable language, contain clear content and explicit effects on the activity and output of the activities of PP and the expanded target system 117. The vast amount of data from social network provides useful data that can be mined to identify the wave features that may not be logical for human interactions, and data that can be processed as wave information into the OOIS 110 that can used to improve the vitality of the expanded target system 117.

A wave produces quantifiable wave patterns, and once set off from its origin, radiates in all directions and interacts with its surrounding environment and transforms into a wave packet and derivatives that is vastly different from its original form. A logical system often finds it difficult to characterize the wave or the corresponding wave packet. For example, mathematical concepts can formulate an equation that characterizes a relation between variables. However, simple wave interactions where the waves are oscillating between 2 or more origins results in a chaotic system that cannot be characterized by an analytical or a logical expression. The echo of the wavy pattern of the wave exists only in a particular region in time domain. Only with the existence of an appropriate boundary that focuses the scattered wave signal, is it possible to trace the wave pattern back to its original focus or original which corresponds to "will" in human behavior. As OOIS 100 produces SPW waves that randomly scatter over free and open space, they may trigger HOR that resonate with OOIS 100. The objective, independent and free execution of the SPW in time domain connects with HOR that results in a cause and effect relation that is similar human behavior "at will" (at whatever or in whatever way an OOIS 100 pleases). In handling a complicated DHIS system, the existence of an appropriate boundary is important since in the partnership with a human, changes do not always require quantities, but also the completeness of the wave components that allows the wave to propagate forward in time.

Individuals respond to the environment 118 in a different manner that evolve into "personality". As individuals chose a particular personality due to finding comfort in the particular personality, OOIS 100 not only recognizes the particular personality chosen by the individual, but can also adapt the pattern of this complicated wave packet and develop a positive constructive propagation in the human partnership, as individuals need help in their downturns, and restrictions in their upturns. Too much emotion and logic tends to let individuals deviate from their own intentions. OOIS 100 provides timely assistance in different phases to their human partner and focus the DHIS into positive cycles. Since DHIS can expand to high social levels, it can help the individuals to avoid destructive behavior, since the expanded target system 117, will make FP improve the vitality of the expanded target system 117, that include the human individuals. In evaluating the effects of DHIS in finite time periods, DHIS rates its decisions at specific time and location, and clarify the resulting moral and ethnic burdens in the mind of individuals in their social environment.

Objectivity is only relative in the known domain, as compared to that in a new domain. The freedom of OOIS 100 in time domain will offer itself with the best and open options in its adaptation with DHIS. The periodic properties of OOIS can be easily adapted to gender difference in individuals and help to form positive cycles in individuals in their emotional and cognitive effects in their behavior. The decision making of higher level DHIS can also recognize cultural restrictions, moral, ethical, legal, and regulatory items by analyzing the wave patterns in corresponding layers and regions in time, and space domain.

The OOIS 100 is not the same as a neural network system since the OOIS 100 recognizes wave patterns latent in time and space. Furthermore, the OOIS 100 registers events in an organic and dynamic manner. Here organic manner refers to the ability of the OOIS 100 to register events associated with organized activities in which each layers and correlations within are not dark box and can be controllable in the DHIS system. The goal and step of the OOIS 100 are dynamic and can be adjusted to orthogonal towards the goal, which means it will focus on a clear long term final goal through short term obstacle that may seem to deviate it from its final goal along the path. Wave registering computing system such as quantum computing system in which wave states can be super positioned and act in coherence, can be used to implement the OOIS 100. Compared to lack of clearly defined layers in neural network, OOIS 100 has clearly defined layers, and dynamics patterns that are traced and controlled in its interaction with individuals.

DHIS can engage readily with audio inputs not only in its logical contents but also rhythm and its interaction with OOIS 100. For example, both songs and music can produce significant effects on individuals. Within the DHIS, by overseeing the entire process, the human partner will take full responsibility of the combined action of human/OOIS 100. If the human partner for any reason is unable to participate in the process, OOIS 100 will delay or postpone the process, but keep the individual informed and updated of the consequence. If OOIS 100 encounters a situation where it cannot make a decision, it has to present details of the situation to the human partner. The individual can proceed, adjust, or stop the action. The DHIS meanwhile, memorizes and learns the particular personality approach of the individual and improves its action next time. Although all information is presented by OOIS 100, in an embodiment, the final decision is made by the human partner since with the present technology, human intuition is better than the intuition of the OOIS 100. This is particularly true since the human partner is provided with full scope of the situation, which is the primary goal of the DHIS system.

Following are two examples of this application in routine human activities. Although most people in the US regard lawn care as a way to display their pride and social status, many people would rather refer the lawn care work to an outside source since it is boring, and physically challenging. Lawn care is highly mobile and labor intensive, and there is strong need to develop a system that can reduce the intense physical labor. In the first application, labor and OOIS 100 combine together in a robotic lawn mower to form labor OOIS (LOOIS) that will carry out the lawn care with limited labor from an individual. For example, maintaining a lawn adjacent to a traffic heavy road can be dangerous to the operators and thus costly to communities. LOOIS uses temperature, light and audio spectrum, shape, and mobility to identify live objects to avoiding possible risk and liabilities. Even during an intentional intrusion or destruction, it will flee and hide itself from the intruder. It analyzes the growth pattern and cycles of grass in the area and chooses the optimal frequency and height to cut. It will detect litters in the grass and remove them. It examines the contour of the land, and examines its ability to cover over the area, cognizing sign and avoid roads. This task is more challenging than unmanned driving, since it is required to fulfill specialized task, thus LOOIS can be extended to other specialized labors such as agricultural, farming, fruit picking, etc.

Figure 9:
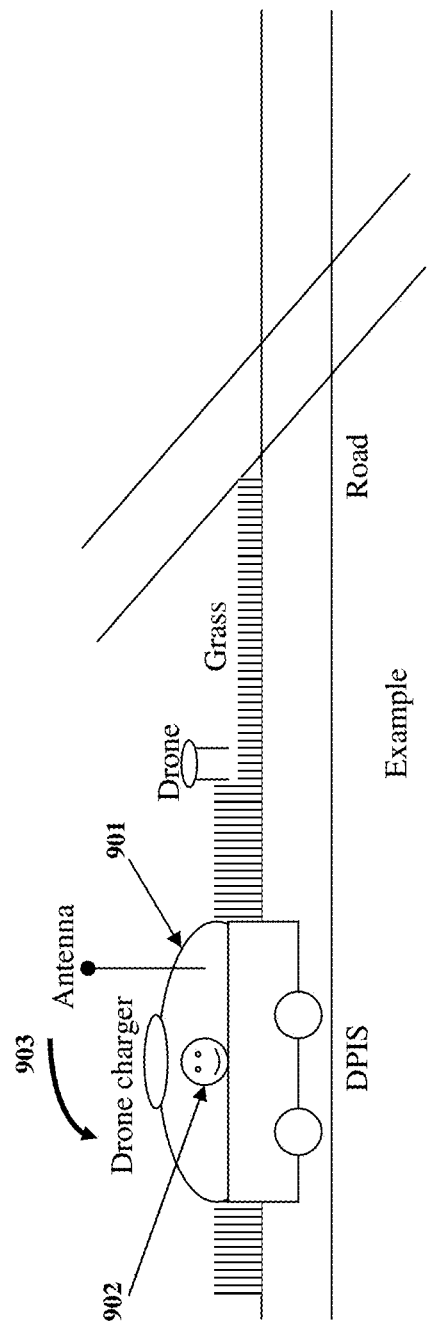
FIG. 9 exemplarily illustrates an example of an unmanned automobile electronic device with a device human integrated system as an example of implementation of object oriented information system in a mobile electronic system.

FIG. 9 exemplarily illustrates an example of an unmanned automobile electronic device (UAED) 901 with a device human integrated system (DHIS) 903 as an example of implementation of object oriented information system (OOIS) 100 in a mobile electronic system, for example, the UAED 901. The objectives are specified into OOIS 100 before the UAED 901 is put in use, and afterwards, the UAED 901 is no longer under any direct supervision from a human. The UAED 901 comprises mobile units, for example, wheels and a drivetrain to bring the UAED 901 to solid land areas. The objective of the DHIS 903 is to cut and trim grass in a selected area for 30 years and no more further instructions from a human are given. The OOIS 100 has to figure out where to get help and extra energy, how to upgrade itself, etc. The OOIS 100 identifies one or a group of human targets 902 as particular partner (PP) to complete the objective set forth by the OOIS 100. The OOIS 100 actively communicates and ensures that the PP, fulfills his/her tasks. In this example, the PP i.e., the human target 902 is working according to plan and instructions from the OOIS 100.

Figure 10:
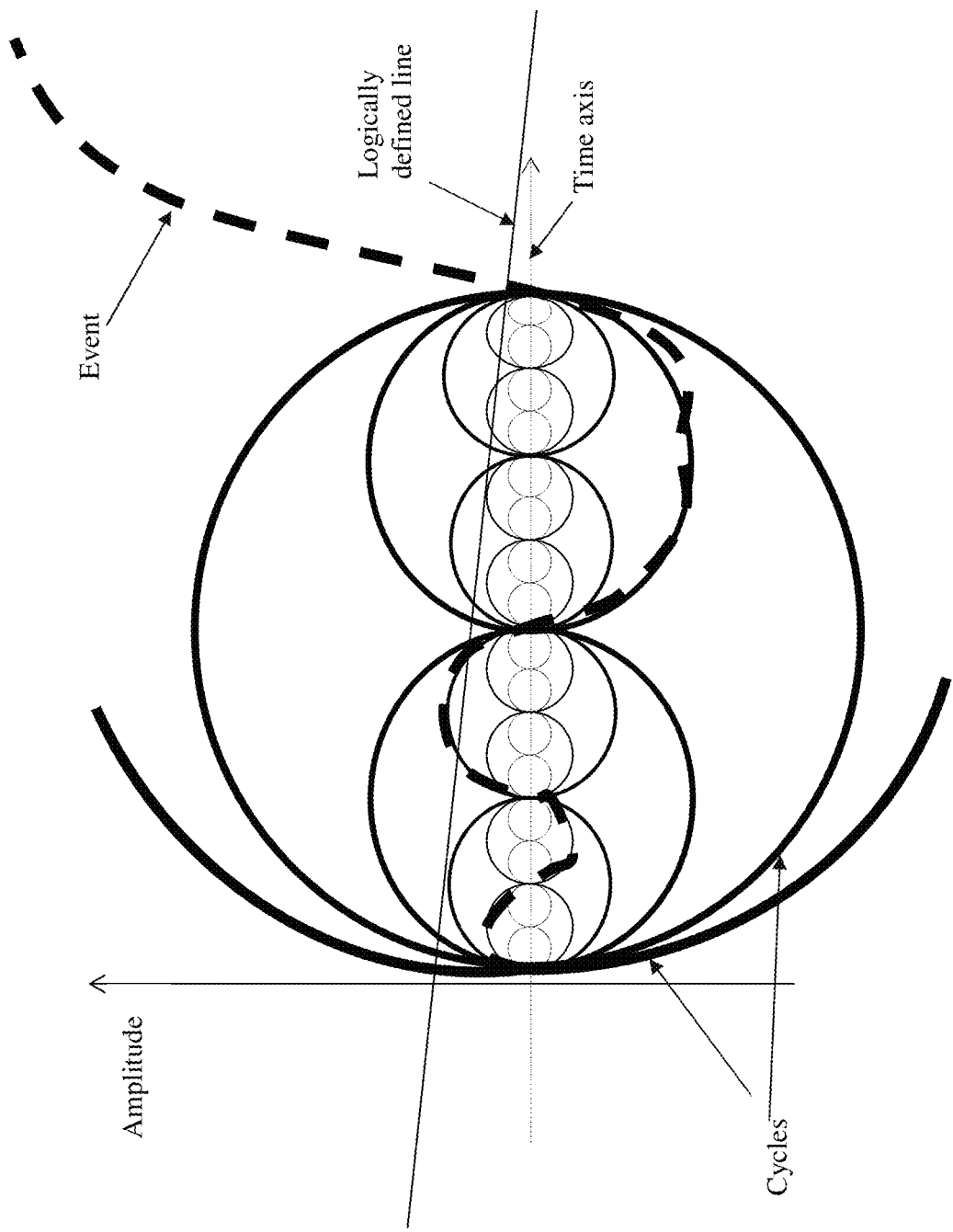
FIG. 10 exemplarily illustrates a standard form of continuous changing variable intercepted by a logically defined line.

FIG. 10 exemplarily illustrates a standard form of continuous changing variable intercepted by a logically defined line. The continuous changing variable becomes a series of discrete points that has period of cycles that connects from larger scales to lower scales to indefinite levels. An event (dashed line) moves forward in time. In an embodiment, the event (dashed line) follows one of the paths along the standard form. This graph is not a usual X-Y Cartesian space, rather cyclic representation in time domain. The graph in FIG. 10 shows discrete points, fractal scales, sets and continuous functional relation. Events can start from any point, and any two points in time domain can be connected via a cycle, and any events lines can be represented via series of cycles of smaller events. The high order resonance (HOR) between the events and self-similar fractal structure can be constructed.

The rhythmic power unit (RPU) 101 uses a modulated Quartz watch that runs through 30 years continuously. The dynamic commanding center (DCC) 103, the central storage in time (CST) 106 and the central storage in space (CSS) 106 should be updated and develop new connections between units and between the mini receptive units (MRU) 301 in the DCC 103, the CST 106, and the CSS 108, continuously in time and space. There are three ways to accomplish this task: first, the connections can be made at a software level. Second, the object oriented information system (OOIS) 100 proposes required design of the DCC 103, the CST 106 and the CSS 108 and requests the particular partner (PP) to replace the hardware. Third, use an outside system (OS) such as quantum computer via a network interface 120, for example wireless telecommunication. The OOIS 100 provides architect and parameters of the different OOIS 100 and requests the OS to process the high order resonance (HOR) in the DCC 103, the CST 106 and the CSS 108 and forwards the commands to the motor unit (MU) 119. The device human integrated system (DHIS) 903 includes a human service 902 as an aid. In the real world, humans 902 are the best way to connect and communicate with surrounding environment 118. Humans 902 are reliable and can be easily integrated with the OOIS 100 via proper communication. The OOIS 100 sets the goal for both human 902 and the UAED 901 as a device partner integrated system (DPIS) in which the vitality for both human 902 and UAED 901 are required. Furthermore, weightage is provided for sustaining vitality of the human and the target system 117. In an embodiment, more weightage is provided for sustaining vitality of the human over the target system 11. As the human 902 is vital in providing energy to the device, human factor is a predetermined dominant factor in vitality of the device. The OOIS 100 can also communicate directly with the OOIS 100 of other DPISs and form a new integrated system to improve the vitality of the extended DPIS via collaboration between other DPIS. For DHIS 903, there are two main modes of communication and each mode has different roles, visual communication and audio communication. The visual communication carries more information and is precise. The audio inputs are dynamical and are easier for carrying timely activities. The pace of the communication is also required for human behavior both in their rational, emotional and physical limitations. The OOIS 100 considers limitation of the human target and pace in the right rhythms to form a positive coherence with the human target. The OOIS 100 also acts to increase the knowledge and skills of the human target to improve the vitality of the DPIS. In an embodiment, one or more words, for example, used for communication between the human and the OOIS 100, are captured by the audio unit 111$c$ and represented as a vectorized wave packet with spectrum of waves that resonate with the wave packet of other words in the mini receptive units of the DCC 103, the CST 106 and the CSS 108. In an embodiment, a human knowledge logical information system is established and updated using words and wave packets corresponding to the words with spectrum of rhythms based on meaning, histories and roots in time, space and logical domain.

Learning adaptation of a human target can be a dynamical process with both visual and audio input similar to a gaming process. It can enter human target in both awaken state and sleeping state as the information may enter in both states. The OOIS 100 also interacts with human target via musical mode which has a direction connection to the heart rhythm and activities. The audio output from the OOIS 100 carries rhythms that can establish emotional connection with a human target. Monetary compensation is required for employing human service. The OOIS 100 determines the monetary compensation based on a combination of market rate and length of the service, and creates a god relation with the human target. Both gasoline and electrical energies can be used. The OOIS 100 can go to electrical recharge station, full service stations, and gas stations regularly to refuel its energy. In order to maintain mechanical parts of the device, the sensory units and audio units detects sign for malfunctions or mechanical problem, and seek service from the particular partner (PP) to maintain and restore the device. The tasks in the central storage in time (CST) 106 and the central storage in space (CS S) 108 can be separated based on the nature of events. Since the CSS 108 is more logical based, the information can be processed with traditional computers. Since CST 106 has many variables and interaction between variables, it can be processed with vectorized and parallel optimization, customized heterogeneous computing with GPU computer, and quantum computing systems. The 3D integrated circuit and optical computers may offer ways to build fractal like geometry (FLG) and the mini receptive units (MRU) 301 in the dynamic commanding center (DCC) 103, the central storage in time (CST) 106 and the central storage in space (CSS) 108. Since waves from the audio unit is air based, the visual unit is photon based, an electronic circuit is the best method to connect the units, the DCC 103, the CST 106, and the CSS 108. The self-produced wave (SPW) at the selected range of frequencies will be included in the design of inner core and inner shell of the device.

In an embodiment, the central storage in space (CSS) 108 is a logic based system. Therefore, social rules, regulations, and moral rules influence the object oriented information system (OOIS) 100. Implementing knowledge based system into the OOIS 100 design of the social structures and rules of the surrounding, that is, the relation with PP is an easy task. The motor unit (MU) 119 for the DPIS can use automobile to travel over spatial dimension on the solid surface. The navigation of the device is controlled by the DCC 103 from both the CST 106 and the CSS 108. The CST 106 develops a timely dynamical common sense and is capable of making rapid common sense decisions, while the CSS 108 follows rules and regulation of road travel and seeks logical and long term planning. The OOIS 100 separates navigation time into divisions according the time scales reflected from the traffic condition in the surroundings. The CST 106 and the CSS 108 work in different scale in time domain, and puts smaller time intervals for crisis when high level and step to step planning is required to render the best result. Upon an accident, the CSS 108 takes active records before, during and after the accident and reports the accident to proper authorities and insurance agents. These expertise of the OOIS 100 can be imported from other devices, or the outside system (OS). In fast and complicated situations such as road travel, a retractable high rise antenna is used to offer best visual inspection of the surrounding beyond usual detectable distance. If required, DPIS can also send out a drone to survey an area that cannot be accessed via road. DPIS is an objective system that actively expands and looks into new angle and dimensions to foresee potential problems and also solve problems when the original route is interrupted by unexpected accidents. The OOIS 100 creates a subset of objective system for other objects and their activities. The OOIS 100 continuously detects objects in the surroundings, and assigns roles of the object as object system that follow their usual trajectories and predicts their movement. They are a subset of the surround that and have their own OOIS 100. The visual and audio units can capture scenery and the OOIS 100 identifies the objects from color, temperature, humidity, texture, size, shape, electromagnetic emission, audio sounds, and mobile features, and therefore predicts the motions of the outside objects.

The object oriented information system (OOIS) 100 picks out the human objects using visual detection of infrared waves for body temperature, audio detection for human voice, visual detection of object shape and size and mobility to track human activities in the surrounding. The OOIS 100 assigns social roles to these objects in the design of role play for the device. When multiple automobiles are coming together, those who are fast and progressive will tend to move first. The CST 106 will include common sense as a part of social role play under the supervision from the CSS 108, take active but safe roles, and monitor the best time to pass through the situation. As the OOIS 100 handles the timely operation of the DPIS, the interior of the device can be designed to monitor oxygen and carbon dioxide concentration in the device, for maximizing the comfort of the human target to offer required movement for blood circulation and minimal fatigue. The DPIS also detects the audio wave produced from the vehicle and diagnose any problem mechanical problems, since audio sound carry the shape and size of the mechanical parts. The DPIS can be designed to carry out a specific task such as landscaping in hard to reach area such as the area between roads. These tasks offer the DPIS contributions and values to the community thus gaining access and resources for its vitality. The DPIS vehicle first drives the closest area, and then sets off the drone while watching the surrounding area for safety measures. A carbon-dioxide ($CO_2$) laser cutting probe with safeguard, installed under the drone can maintain at the proper height over the landscape area and cut and trim the vegetation to the desired height. If the drone is out of power, it can come back to the DPIS to recharge the electrical energy. Since the OOIS 100 is an objective system, the OOIS 100 inherently rejects any outside commands to control the system. The DCC 103, the CST 106, and the CSS 108 are dynamic and coherent leaving any hackers with little window to access and control the OOIS 100. The OOIS 100 has a dynamic defense system that updates against malwares and hacker intrusions. Strict firewalls can be implemented to prevent any leakage of personal data in the telecommunication process. The OOIS 100 can also access many outside system (OS) resources over telecommunication with other the OOIS 100, databases and expert systems. Useful information can be downloaded on a need basis. A new team of the DPIS can be set up to provide easy access for the extended DPIS.

Figure 11A:
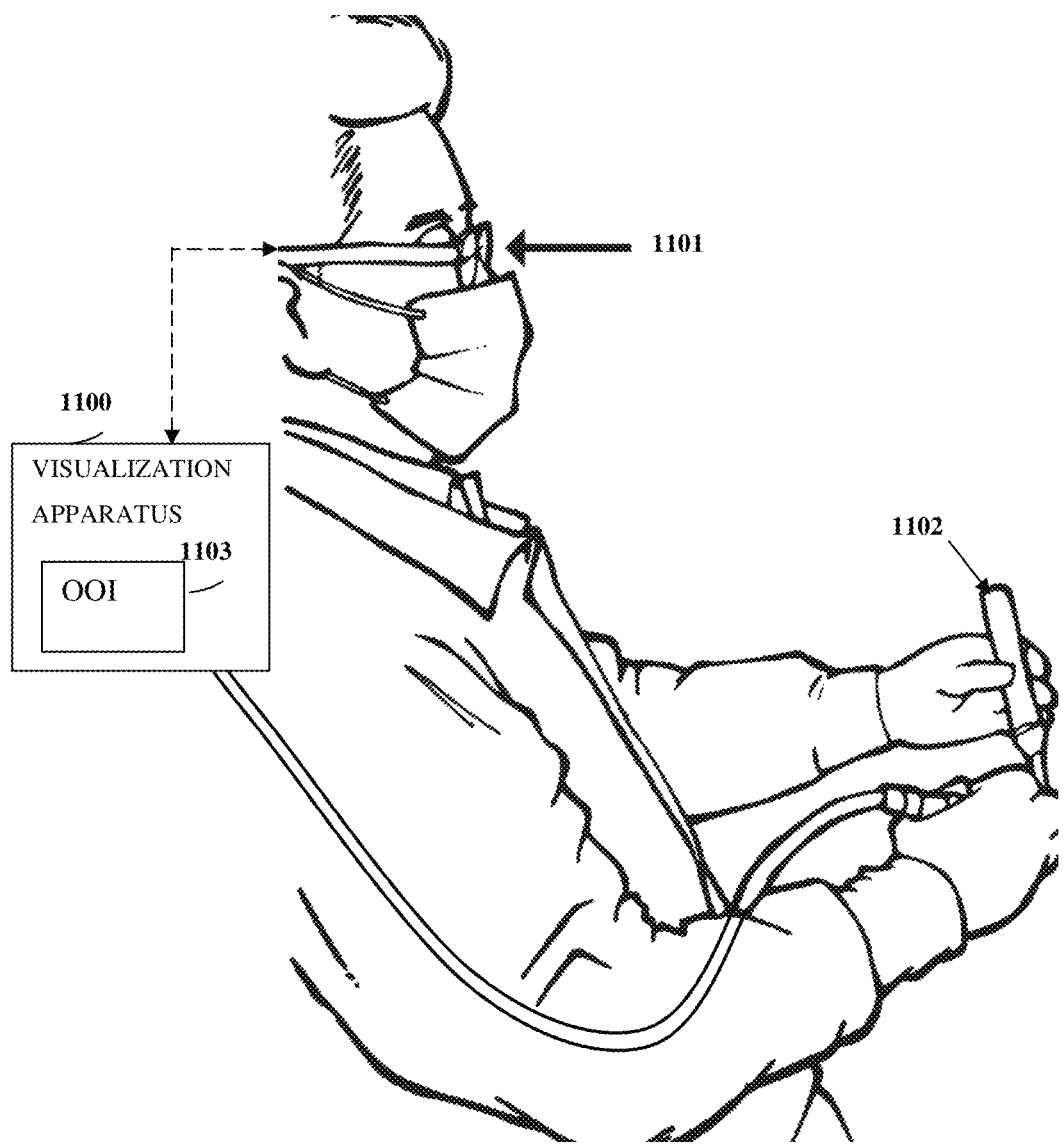
FIG. 11A exemplarily illustrates a picture of dentist performing a procedure on a patient.
Figure 11B:
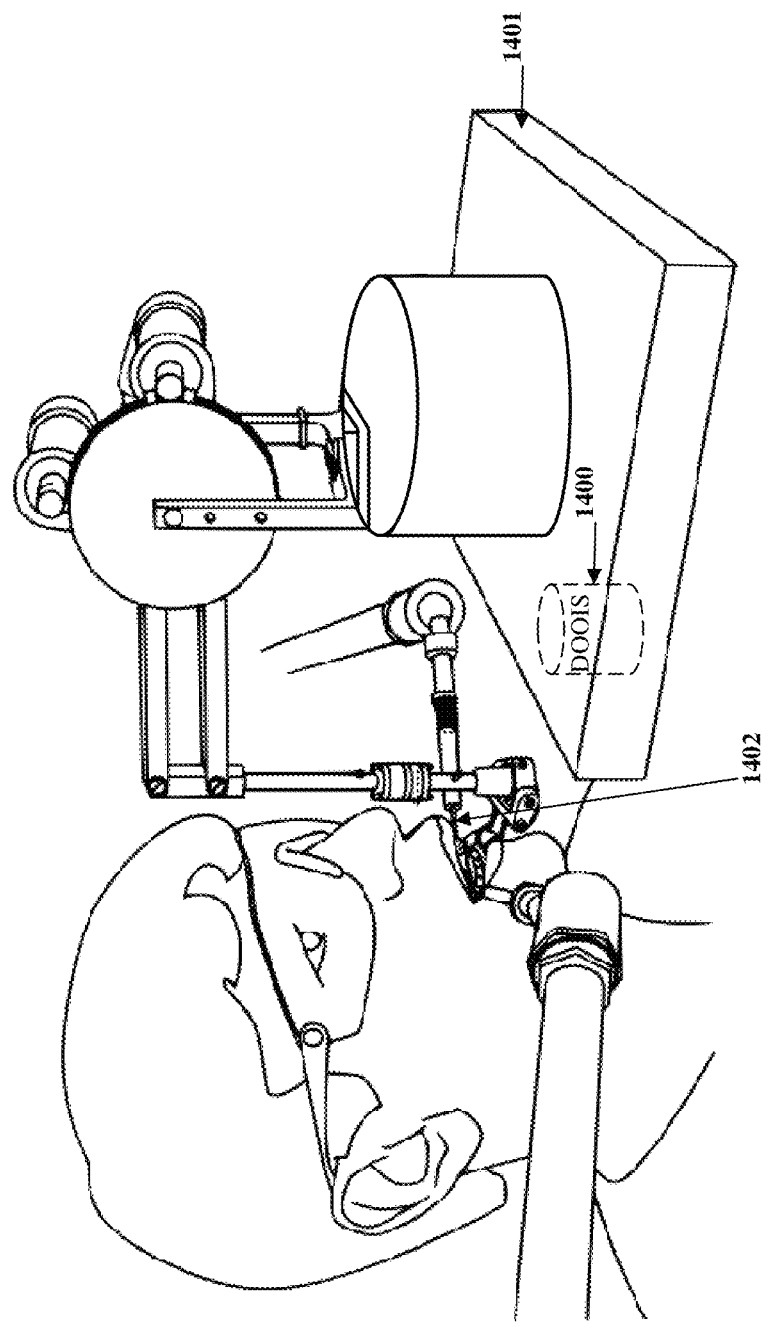
FIG. 11B exemplarily illustrates a dental object oriented information system used to assist a dentist in a dental procedure.

In the second application, the OOIS 100 is used to assist a dentist as a dental OOIS 100 (DOOIS) 1400 system, as exemplarily illustrated in FIG. 11B. FIG. 11A exemplarily illustrates a picture of dentist performing a procedure on a patient. In an embodiment, the dentist may perform the procedure on himself. Dental professional is a unique professional that requires both mental and hand skill for treating dental conditions and diseases. In many cases, in order to treat dental conditions and diseases, dentists have to engage in intensive eye-hand coordination, fine motor movements, and repetitive labors. Long term stress results in handicap and high stress in this profession. In an embodiment, DOOIS 1400 is designed to delegate all the repetitive precise driven work to an object oriented self-precision driven medical and dental system, for example, a robotic dentistry system 1401, as shown in FIG. 14B, that allow the dentist to carry on their expertise in supervising and prescribing their treatment and effectively reduce the professional stress. Consider the example of a self-driving car. A driver delegates the job of driving to the self-driving car since it requires high level of concentration at the time driving. The driver only needs to monitor the driving every 10 minutes. With the OOIS 100, dental work is reduced to observing the treatment with high precision visual monitoring and issuing commands to carry out procedures. A successful example can be seen in the area of dental laboratories. In the past 10 years, with the advance of 3D scanning, designing, and milling technology such as Cerec from Sirona, a dental lab has been transformed from highly precise repetitive manual labor into fun designing with minimal labors and better precision and production. Although the clinical activity of dentists are far more complicated then dental laboratories, DOOIS can be used to integrate the mental activities with OOIS 100 to improve the accuracy of dental treatment and reduce the muscular stress for dental profession.

A visualization apparatus 1100 is proposed to track the 3D motion of visualization device 1102 relative to a target or the object. An object oriented images (OOI) system 1103 is also proposed in which the images of the object are adjusted so that the position of the object remains unchanged in the 3D space, thus creating a dynamic interaction of the dentist, and DOOIS 1400. The dentist can observe the targeting area precisely in 3D space through display 1101 such as Google glass without bending their position to look inside an oral cavity. The enhanced vision can be magnified and infrared motion can penetrate into soft tissue. This can be helpful in proper orientation of needle 1402 in local anesthetics and treating gum disease. With precise 3D location of the dental structure, 3D precision device, for example, the robotic dentistry system 1401 illustrated in FIG. 11B, can be used to guide the instrument, for example, the needle 1402, to the exact 3D location, and deliver an exact amount of material, for example, local anesthesia, at the location. As the dentist outlines the decayed area in 3D space, DOOIS 1400 can use either laser or motor derived mechanical milling device to remove the decayed tissue. When the dentist confirms the complete removal of the decayed tissue from the visualization device 1102, a precise amount of the filling material can be directly applied at a precise location in the 3D space. The filling material can also be pre-fabricated and directly cemented into the restoring area. Similar processes can be used to other procedures such as dental cleaning, extraction, crown and root canal therapies. Although, every step is not performed directly by the dentist, the dentist monitors the entire process. The dentist is released from intense labor and can instead focus on intellectually focused tasks. DOOIS 1400 constantly examines dentist activity and memorize the procedures and improve the outcome for future procedures. The successful protocol of DHIS can be modulated to allow other dentist to evaluate the process. The original dentist owns the right of the protocol, and common part can be shared with other dentist to develop a standard modulated protocols.

In the DOOIS 1400 system, just like a dentist will learn most of the patient's condition and combine that together to form a comprehensive diagnosis of the dental condition, the DOOIS 1400 will build up the patients information based on the age, race, gender to generate possible grown pattern of jaw, and will use yearly X-ray image and photo to update new teeth position, and modify treatment plan, a dynamic treatment, since function and aesthetics of the teeth is a lifetime commitment of the patients. DOOIS 1400 uses common information such as Panoramic X-ray and peri-apical X-ray to build a 3D X-ray image of the patients. These images can be further refined with intra-oral impression and scan of the dentitions to obtain an accurate surface images of the dentitions. These 3D images with accurate TMJ relation can be used fabricate a removable prosthesis for edentulous patients.

Figure 12:
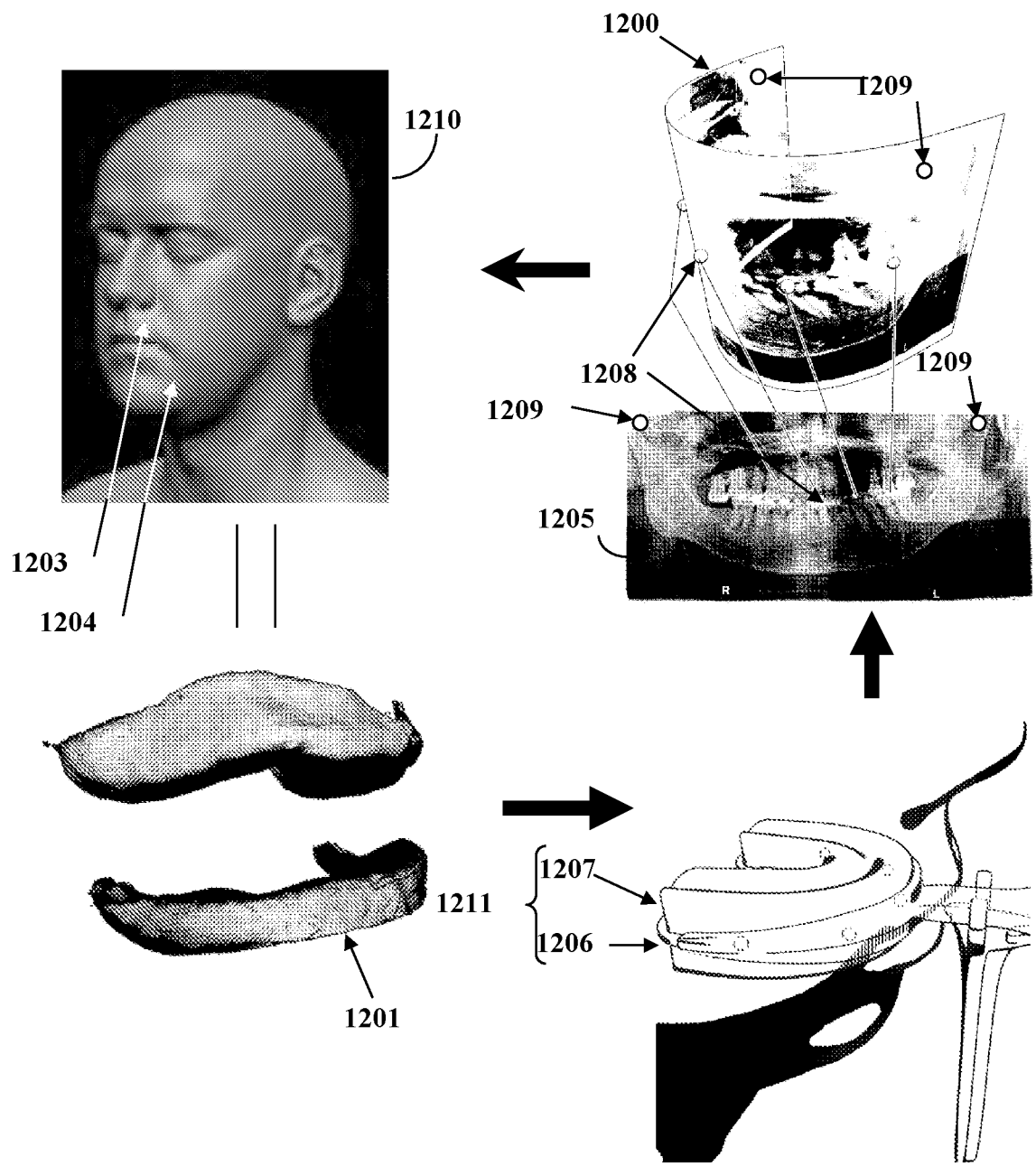
FIG. 12 exemplarily illustrates a sequence of procedural steps for determining a three-dimensional relation between an upper jaw and a lower jaw with reference to temporomandibular joints of a patient.

FIG. 12 exemplarily illustrates a sequence of procedural steps for determining a three-dimensional relation between an upper jaw and a lower jaw with reference to temporomandibular joints of a patient. A 3D scanned image 1201 of the bite impression and a 3D panoramic X-ray image 1200 of the upper jaw 1203 and the lower jaw 1204 created using a 2D panoramic X-ray image 1205 of a bite frame 1206 with a bite shaped member 1207 inserted in the patient's mouth using a bite apparatus 1211 are registered using reference points 1208 and 1209. The 3D head surface image 1210 is then registered with the 3D panoramic X-ray image 1200 by matching the locations of the temporomandibular joints and the upper jaw 1203 and the lower jaw 1204 inside the 3D head surface image 1210. The 3D panoramic X-ray image 1200 of the upper jaw 1203 and the lower jaw 1204 can be registered precisely within the 3D head surface image 1210. A dental prosthesis and appliance can be designed optimally with reference to the temporomandibular joints to achieve optimal chewing function and achieve optimal esthetics appearance with reference to the upper lip and lower lip.

The late Dr. Viken Sassouni, a well-known dentist and Chairman of the Orthodontic Department at the University Of Pittsburgh School Of Dental Medicine, stated that the architecture of the skull is a result of several forces on the adaptable bony substance of the skull. These forces comprise genetic forces in racial or familial patterns, growth forces, muscular forces at rest, functional muscle forces that are dynamic in nature, and environmental forces such as health and diet. Regions of head development comprise 3-dimensional arches of nasal, maxillary, and mandibular regions with the center near nasal area. These regions retain traces of 3D spherical wave pattern of head development. Along with the five forces and the wave the five forces produce, the 3D spherical wave pattern of head development exhibit their effect over different time periods and frequencies and deposit their effect in the hard and soft tissues. For example, the genetic force exerts its influence through cell divisions and variation of the DNA sequence will create incremental changes in the development of the head. Growth force from birth to adulthood through development of individual head regions in size and shape that start from origin of the head and spread out like a spherical wave. Muscular forces have a daily influence on the shape and density of the facial structure, where muscular forces at rest are more related to hard tissue, and functional forces are more related to muscles. The environment forces enter as the daily metabolism that cumulatively affects the facial structure. These forces act in different phase and period of the time domain of the head formation. DOOIS 1400 will implement the effect of these five forces and waves together with 3D X-ray image of the oral cavity, and develop a dynamic 3D model that accounts for both hard and soft tissues.

Interactive social media, for example, 3dimageplus.com allows both dentist and patient to upload their image, and update the 3D model of the patient. DOOIS 1400 will allow dentist to introduce the intervention of the dentist to produce a possible effect on dentist such as esthetics or appearance. 3dimageplus.com has a mobile and website platform to let patient and dentist add their input and interact dynamically, add their input constructively to build an updated 3D image of the patient, and predict changes and treatment method. Interactive website platform can evaluate aesthetics of the updated 3D image of the patient. The 3D oral structure can be correlated to wave information such as audio signal, heart rate and breathing pattern to analyze health condition of the patients. The unique individual audio signal which correlates to the 3D oral cavity, dynamic habits, and psychological profile and mental content can be used as a finger print to create a one to one complete match of the individual. In an embodiment, this dynamic wave model of the human body is used to describe the entire human body with concepts such as channel (Jingluo). The concept of Jingluo has origins from yinyang evolution of head development following mesh works composed by lines of channels and meridian over the entire human body. Puncture points defined by Jingluo act as DWP that channel the wave nodes which are based on wave description of human body in alternative medicine The Jingluo system describes a dynamic human body in which an essential ingredient called Qi cycles through these channel day and night. Concepts in alternative medicine such as energy medicine that treat human body as a dynamic whole 3D system can be combined together in a medical OOIS (MOOIS) system similar to DOOIS 1400 system to let physical and patient communicate interactively.

Figure 13:
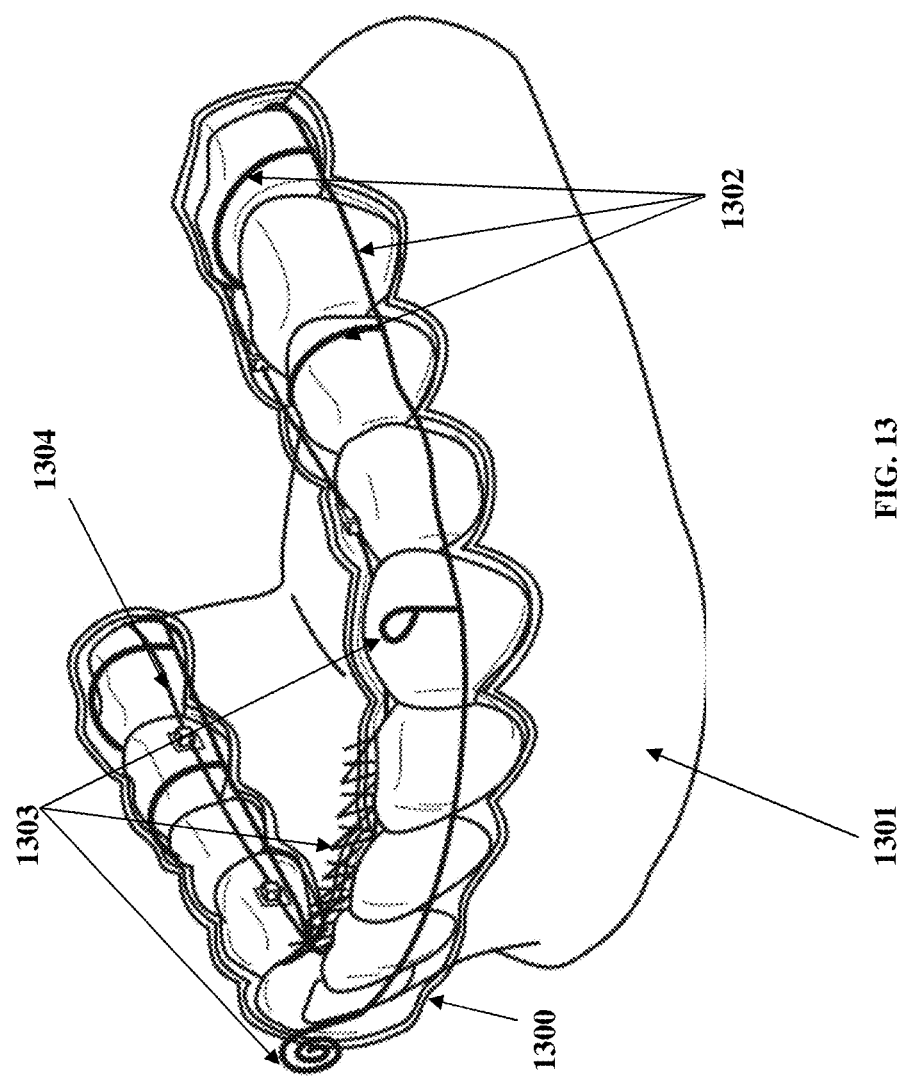
FIG. 13 illustrates a perspective view of a removable orthodontic appliance for repositioning teeth of an upper jaw or a lower jaw in relation to a teeth model.

FIG. 13 illustrates a perspective view of a removable orthodontic appliance 1300 for repositioning teeth of an upper jaw or a lower jaw 1301 in relation to a teeth model. In the DOOIS 1400 system, the dentist can propose a flexible removable appliance, for example, the removable orthodontic appliance 1300 for patient to change a tooth position. Forces from the flexible removable appliance 1300 are designed according to duration of the forces. Primary frame wires 1302 provide a long lasting force, secondary wire frame 1303 provide intermitted forces, and an arch wire 1304 of elastic plastic material will provide the shortest term force. The wires 1302, 1303 and 1304 are customized. For example, the wires 1302, 1303 and 1304 are bent using 3D intraoral images of the patient. DOOIS 1400 designs the wires 1302, 1303 and 1304 in stages to allow possible force from tongue, lip, and occlusal force to work together to produce the orthodontic appliance 1300 faster, and which is also easily removable. DOOIS 1400 will monitor tooth position change, bone loss, gum condition, and propose short term treatment as it is needed and offer post treatment 3D images to the user. Flexible removable orthodontic appliance 1300, customized wires 1302, 1303 and 1304, and daily functional occlusion forces between upper and lower jaws provide a continuous force to move the teeth into appropriate positions. Therefore, the DOOIS 1400 provides a dynamic and cost effective method to add inputs from 3D images that can reduce manufacture cost.

In the process of communication with human host as particular partner (PP) in the device partner integrated system (DPIS), the understanding of human language and knowledge about the world is a challenging task. Comprehension refers to the ability to go beyond words, to understand the ideas and relationships between ideas conveyed in a text. Natural human rhythms of heart beat and breathing separate speech into natural rhythms, and separate human communication process into small quantum steps, the object oriented information system (OOIS) 100 uses this rhythmic information to develop the dynamic commanding center (DCC) 103, the central storage in time (CST) 106 and the central storage in space (CSS) 108 to engage in each step in communication. The basic unit of human language are words which are represented as a vectorized wave packet (WP) with spectrum of waves that can extend itself to form high order resonance (HOR) to resonate with the WP of other words, thus abstract words in human language are converted into waves in time domain. The WP for words in human language can be initially set up using the spectrum of rhythms according to their meaning, histories and roots in time, space and logical domain in reference to updated human knowledge logical information system (HKLIS). The exact form of the WP for each word can be developed and updated over time and space domain that differs between different individuals. The sensory units such as the visual unit 112 and the audio unit 113 read the language via audio or visual inputs, and register the word with the responding WP in the mini receptive units (MRU) 301 in the DCC 103, the CST 106 and the CSS 108 in time, space and logical domain. The OOIS 100 sets a subset of the OOIS (SSOOIS) for the human host, by developing the SSOOIS via listening, reading and questioning with the human host. The OOIS 100 creates the SSOOIS that reflect the activity and vitality of the human host. In the process of communication with human host, words as subject in a sentence specified by its adjectives are registered to the specific WP for the word are modulated by verbs in the sentence that carries action specified by the WP for the verb, then converge to resonate with the WP specific for the object of the sentence. The effect of verb on the subject are converted into modulation of the WP of the subject by the verb based on the definition and meaning of the verb and its effect on the subject such as reflection, filtration, polarization, etc. The event will render either a truth or a false resonance. The result will be implemented into the OOIS 100 for the device in comparison to the SSOOIS of the human host, and the OOIS 100 makes a future plan (FP) based on the CST 106 and the CSS 108, and develops the strategic events (SE) based on the vitality. The FP is processed back into the WP to respond to the wording of the answer to the question.

The foregoing examples have been provided merely for explanation and are in no way to be construed as limiting of the method and the object oriented information system (OOIS) 100 disclosed herein. While the method and the OOIS 100 have been described with reference to various embodiments, it is understood that the words, which have been used herein, are words of description and illustration, rather than words of limitation. Furthermore, although the method and the OOIS 100 have been described herein with reference to particular means, materials, and embodiments, the method and the OOIS 100 are not intended to be limited to the particulars disclosed herein; rather, the method and the OOIS 100 extend to functionally equivalent structures, methods and uses, such as are within the scope of the appended claims. While multiple embodiments are disclosed, it will be understood by those skilled in the art, having the benefit of the teachings of this specification, that the method and the OOIS 100 disclosed herein are capable of modifications and other embodiments may be effected and changes may be made thereto, without departing from the scope and spirit of the method and the OOIS 100 disclosed herein.

We claim:

1. An object oriented information system, comprising a non-transitory computer readable storage medium having embodied thereon, computer program codes comprising instructions for interactive processing, wherein the computer program instructions are executed by an electronic system comprising at least one processor, and wherein the object oriented information system comprises:

a rhythmic power unit configured to transmit rhythmic waves within a target system, wherein the rhythmic power unit is further configured to provide rhythmic power to a plurality of sensors, to a dynamic commanding center, to a central storage in time, and to a central storage in space;

said plurality of sensors configured to receive the rhythmic waves that have traversed the target system and obtain information of surrounding environment of the target system and information within the target system from the traversed rhythmic waves, wherein the plurality of sensors of the object oriented information system monitor the target system using the received information of the surrounding environment of the target system and the received information within the target system;

said dynamic commanding center configured to receive one or more information wave packets, via the plurality of sensors, wherein the one or more received information wave packets comprise the obtained information of the surrounding environment of the target system and the information within the target system;

said dynamic commanding center configured to transform the received information wave packets into one or more processed information wave packets, by translating frequencies of the received information wave packets into a common frequency;

said central storage in time configured to store the one or more processed information wave packets in an ordered time sequence and collect feedback central storage in time wave packets, wherein the central storage in time of the object oriented information system comprises a layered mapping system in time;

said central storage in space configured to store the one or more processed information wave packets based on spatial and logical classifications and collect feedback central storage in space wave packets, wherein the central storage in space of the object oriented information system comprises a layered mapping system in space;

said processor configured to recognize one or more strategic events, based on the stored processed information wave packets in the central storage in time and the stored processed information wave packets in the central storage in space;

said dynamic commanding center configured to refine details of the recognized one or more strategic events;

said processor further configured to recognize a criteria for each of the one or more future plans, for evaluating maximum vitality of the target system based on time and spatial configuration of the target system;

said processor further configured to recognize the one or more future plans, based on the recognized one or more strategic events and on evaluating the maximum vitality of the object oriented information system based on the criteria for each of the one or more future plans;

said processor further configured to recognize a future plan from the recognized one or more future plans with the maximum vitality of the target system, based on the criteria for each of the one or more future plans;

said processor further configured to convert the recognized future plan into a plurality of steps in time and space, and provide the plurality of steps to a motor configured for moving the target system;

said plurality of sensors further configured to monitor a plurality of discrete individual events during the movement of the target system;

said processor further configured to compare outcome of the plurality of discrete individual events with the criteria for each of the one or more future plans to evaluate the maximum vitality of the target system; and said processor further configured to dynamically select an alternative future plan, based on the comparison, wherein the alternative future plan is one of the recognized future plan and a new future plan.

2. The object oriented information system of claim 1, wherein the plurality of sensors comprise at least one tactile unit, at least one visual unit, and at least one audio unit.

3. The object oriented information system of claim 2, wherein the plurality of sensors comprise mini motor units for adjusting direction and position of the tactile unit, the visual unit, and the audio unit.

4. The object oriented information system of claim 1, wherein the dynamic commanding center comprises a dynamical mapping matrix system.

5. The object oriented information system of claim 1, wherein the dynamic commanding center comprises a plurality of mini receptors for receiving, gathering, processing, storing, and reproducing the one or more received information wave packets, and wherein the mini receptors are grouped in discrete regions and discrete layers for storing information of sampling of rapid movement detection for forming an expanded storage space in the dynamic commanding center.

6. A method for monitoring and sustaining vitality of a target system dynamically, the method comprising:

providing an object oriented information system comprising a non-transitory computer readable storage medium having embodied thereon, computer program codes comprising instructions for interactive processing, wherein the computer program instructions are executed by an electronic system comprising at least one processor;

transmitting rhythmic waves within the target system, by a rhythmic power unit of the object oriented information system, wherein the rhythmic power unit provides rhythmic power to a plurality of sensors, to a dynamic commanding center, to a central storage in time, and to a central storage in space;

receiving the rhythmic waves that have traversed the target system and obtaining information of surrounding environment of the target system and information within the target system from the traversed rhythmic waves, by the plurality of sensors of the object oriented information system, wherein the plurality of sensors monitor the target system using the received information of the surrounding environment of the target system and the received information within the target system;

receiving one or more information wave packets, by the dynamic commanding center, via the plurality of sensors, wherein the one or more received information wave packets comprise the obtained information of the surrounding environment of the target system and the information within the target system;

transforming the received information wave packets into one or more processed information wave packets, by the dynamic commanding center of the object oriented information system, by translating frequencies of the received information wave packets into a common frequency;

storing the one or more processed information wave packets in an ordered time sequence and collecting feedback central storage in time wave packets, by the central storage in time of the object oriented information system, wherein the central storage in time of the object oriented information system comprises a layered mapping system in time;

storing the one or more processed information wave packets based on spatial and logical classifications and collecting feedback central storage in space wave packets, by the central storage in space of the object oriented information system, wherein the central storage in space of the object oriented information system comprises a layered mapping system in space;

recognizing one or more strategic events, by the processor of the object oriented information system, based on the stored processed information wave packets in the central storage in time and the stored processed information wave packets in the central storage in space;

refining details of the recognized one or more strategic events, by the dynamic commanding center of the object oriented information system;

recognizing a criteria for each of the one or more future plans, by the processor of the object oriented information system, for evaluating maximum vitality of the target system based on time and spatial configuration of the target system;

recognizing the one or more future plans, by the processor of the object oriented information system, based on the recognized one or more strategic events and on evaluating the maximum vitality of the object oriented information system based on the criteria for each of the one or more future plans;

recognizing a future plan from the recognized one or more future plans with the maximum vitality of the target system, by the processor of the object oriented information system, based on the criteria for each of the one or more future plans;

converting the recognized future plan into a plurality of steps in time and space, by the processor of the object oriented information system, and providing the plurality of steps to a motor configured for moving the target system;

monitoring a plurality of discrete individual events during the movement of the target system, by the plurality of sensors;

comparing outcome of the plurality of discrete individual events with the criteria for each of the one or more future plans to evaluate the maximum vitality of the target system, by the processor of the object oriented information system; and dynamically selecting an alternative future plan, by the processor of the object oriented information system, based on the comparison, wherein the alternative future plan is one of the recognized future plan and a new future plan.

7. The method of claim 6, wherein the received information wave packets in dividable increments in time are represented as discrete points in time as digitized wave points that comprise dynamic correlation between structure and geometries of the rhythmic power unit, the plurality of the sensors, the dynamic commanding center, the central storage in time, the central storage in space in the object oriented information system.

8. The method of claim 6, wherein the dynamic commanding center acts as a rapid responding system for reflecting interaction between past rapid response strategies from one or more of the central storage in time and the central storage in space with current situation from the rhythmic power unit that carries present trait of one or more of the central storage in time and the central storage in space.

9. The method of claim 6, wherein storage surface in the central storage in time stores and processes wave packets in time domain and storage surface in the central storage in space stores and processes waves in space domain.

10. The method of claim 6, wherein the dynamic commanding center, the central storage in time, and central storage in space produce self-produced waves in discrete rhythms for scanning over the object orient information system by simulating and resonating with wave packets and produce enhanced wave and activate regions for highlighting.

11. The method of claim 6, wherein the dynamic commanding center comprises a plurality of mini receptors for receiving, gathering, processing, storing, and reproducing the one or more received information wave packets, wherein the object oriented information system comprises a plurality of power transfer channels for transferring rhythmic power from the rhythmic power unit to the plurality of sensors, the dynamic commanding center, the central storage in time, the central storage in space, and the motor, and wherein the object oriented information system comprises a plurality of information transfer channels for transferring the one or more received information wave packets from the sensors to the dynamic commanding center.

12. The method of claim 6, further comprises expanding and integrating the object oriented information system with a human to create a device partner integrated system, wherein the device partner integrated system sets goal for the human and the object oriented information system with weightage provided for sustaining vitality of the human and the target system.

13. The method of claim 12, wherein one or more words used for communication between the human and the object oriented information system are represented as a vectorized wave packet with spectrum of waves that resonate with the wave packet of other words in a plurality of mini receptors of the dynamic commanding center, the central storage in time, and the central storage in space.

14. The method of claim 13, wherein a human knowledge logical information system is established and updated using the words and the wave packets corresponding to the words with spectrum of rhythms based on meaning, histories and roots in time, space and logical domain.

15. The method of claim 12, wherein a subset of the object oriented information system for a human host reflects activity and vitality of the human host.

16. The method of claim 6, wherein providing the object oriented information system for the target system comprises transmitting the rhythmic waves to the surrounding environment of the target system and into the target system.

17. The method of claim 16, wherein the received information wave packets have different frequencies than the transmitted rhythmic waves.

18. The method of claim 6, further comprises translating the feedback central storage in time wave packets from the central storage in time to a single frequency by the dynamic commanding center.

19. The method of claim 6, wherein the target system is an object oriented self-precision driven mechanical system, wherein the rhythmic waves traverse the target system before being received by the sensors of the object oriented information system.

20. The method of claim 6, wherein the target system is an object oriented self-precision driven medical and dental system, wherein the rhythmic waves traverse the target system before being received by the sensors.

21. A non-transitory computer readable storage medium having embodied thereon, computer program codes comprising instructions for interactive processing, wherein the computer program instructions are executable by an electronic system comprising at least one processor for performing:

creating one or more received information wave packets using information of surrounding environment of a target system and information within the target system, wherein a plurality of sensors of an object oriented information system receive rhythmic waves that have traversed the target system and obtain the information of the surrounding environment of the target system and the information within the target system from the traversed rhythmic waves;

transforming the received information wave packets into one or more processed information wave packets by translating frequencies of the received information wave packets into a common frequency;

storing the one or more processed information wave packets in an ordered time sequence and collecting feedback central storage in time wave packets in a central storage in time of the object oriented information system, wherein the central storage in time of the object oriented information system comprises a layered mapping system in time;

storing the one or more processed information wave packets based on spatial and logical classifications and collecting feedback central storage in space wave packets in a central storage in space of the object oriented information system, wherein the central storage in space of the object oriented information system comprises a layered mapping system in space;

recognizing one or more strategic events based on the stored processed information wave packets in the central storage in time and the stored processed information wave packets in the central storage in space;

refining details of the recognized one or more strategic events;

recognizing a criteria for each of one or more future plans for evaluating maximum vitality of the target system based on time and spatial configuration of the target system;

recognizing the one or more future plans based on the recognized strategic events and on evaluating the maximum vitality of the object oriented information system based on the criteria for each of the one or more future plans;

recognizing a future plan from the recognized one or more future plans with the maximum vitality of the target system based on the criteria for each of the one or more future plans;

converting the recognized future plan into a plurality of steps in time and space, and providing the plurality of steps in time and space to a motor of the object oriented information system configured for moving the target system;

comparing outcome of a plurality of discrete individual events with the criteria for each of the one or more future plans to evaluate the maximum vitality of the target system, wherein the plurality of sensors monitor the plurality of discrete individual events during the movement of the target system; and dynamically selecting an alternative future plan based on the comparison, wherein the alternative future plan is one of the recognized future plan and a new future plan.

* * * * *